US010357230B2

(12) United States Patent
Bolduc

(10) Patent No.: US 10,357,230 B2
(45) Date of Patent: Jul. 23, 2019

(54) DEVICES, SYSTEM, AND METHODS FOR GUIDING AN OPERATIVE TOOL INTO AN INTERIOR BODY REGION

(71) Applicant: Medtronic Vascular, Inc., Minneapolis, MN (US)

(72) Inventor: Lee Bolduc, Redwood City, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 358 days.

(21) Appl. No.: 15/071,501

(22) Filed: Mar. 16, 2016

(65) Prior Publication Data
US 2016/0193450 A1 Jul. 7, 2016

Related U.S. Application Data

(60) Continuation of application No. 11/254,619, filed on Oct. 20, 2005, now Pat. No. 9,320,503, which is a (Continued)

(51) Int. Cl.
*A61B 17/00* (2006.01)
*A61B 17/064* (2006.01)
(Continued)

(52) U.S. Cl.
CPC ...... *A61B 17/00234* (2013.01); *A61B 17/064* (2013.01); *A61B 17/068* (2013.01);
(Continued)

(58) Field of Classification Search
CPC ........... A61M 25/0136; A61B 17/0401; A61B 17/0409; A61B 17/064; A61B 17/068;
(Continued)

(56) References Cited

U.S. PATENT DOCUMENTS 2,033,039 A 3/1936 Limpert
3,499,222 A 3/1970 Linkow et al.
(Continued)

FOREIGN PATENT DOCUMENTS

AU 2002353807 B2 6/2003
AU 2004277897 B2 4/2005
(Continued)

OTHER PUBLICATIONS

"Australian Application Serial No. 2002351188, Office Action dated Dec. 8, 2008", 3 pgs.
(Continued)

*Primary Examiner* — Alexander J Orkin

(57) ABSTRACT

A guide device establishes a guide passage through a guide tube, through which an operative tool can be deployed into an interior body region for use. A steering assembly, in use, deflects or bends the distal end region of the guide tube, so that the operative tool can be placed in a desired orientation with respect to tissue. The steering assembly is desirable configured for single handed operation by the clinician. The steering assembly is also desirably configured to provide a mechanical advantage sufficient to translate relatively small increments of clinician control into relatively larger increments of guide tube deflection. In one arrangement, the steering assembly includes a rack and pinion linkage system. In another arrangement, the steering assembly includes a pivoting lever system.

8 Claims, 9 Drawing Sheets

Related U.S. Application Data continuation-in-part of application No. 11/166,411, filed on Jun. 24, 2005, now Pat. No. 8,092,519, which is a division of application No. 10/271,334, filed on Oct. 15, 2002, now Pat. No. 6,960,217, said application No. 11/254,619 is a continuation-in-part of application No. 10/307,226, filed on Nov. 29, 2002, now Pat. No. 8,075,570, and a continuation-in-part of application No. 10/669,881, filed on Sep. 24, 2003, now Pat. No. 7,491,232.

(60) Provisional application No. 60/333,937, filed on Nov. 28, 2001.

(51) Int. Cl.
  *A61B 17/068* (2006.01)
  *A61B 17/34* (2006.01)
  *A61M 25/01* (2006.01)
  *A61B 90/00* (2016.01)
  *A61B 17/04* (2006.01)

(52) U.S. Cl.
  CPC ...... *A61B 17/3415* (2013.01); *A61B 17/3468* (2013.01); *A61M 25/0136* (2013.01); *A61M 25/0147* (2013.01); *A61B 17/0401* (2013.01); *A61B 2017/003* (2013.01); *A61B 2017/00327* (2013.01); *A61B 2017/0409* (2013.01); *A61B 2017/0441* (2013.01); *A61B 2017/0649* (2013.01); *A61B 2090/3966* (2016.02); *A61M 2025/015* (2013.01)

(58) Field of Classification Search
  CPC ............ A61B 17/3415; A61B 17/3468; A61B 17/00234
  See application file for complete search history.

(56) References Cited

U.S. PATENT DOCUMENTS

| | | |
|---|---|---|
| 3,686,740 A | 8/1972 | Shiley |
| 3,799,172 A | 3/1974 | Roman |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,694,827 A | 9/1987 | Weiner et al. |
| 4,781,682 A | 11/1988 | Patel |
| 4,822,345 A | 4/1989 | Danforth |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski |
| 5,192,314 A | 3/1993 | Daskalakis |
| 5,195,968 A | 3/1993 | Lundquist et al. |
| 5,199,950 A | 4/1993 | Schmitt et al. |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,352,197 A | 10/1994 | Hammersmark et al. |
| 5,364,351 A | 11/1994 | Heinzelman et al. |
| 5,383,880 A | 1/1995 | Hooven |
| 5,387,235 A | 2/1995 | Chuter |
| 5,396,902 A * | 3/1995 | Brennen ............ A61M 25/0136 600/585 |
| 5,409,498 A | 4/1995 | Braddock et al. |
| 5,456,713 A | 10/1995 | Chutter |
| 5,456,714 A | 10/1995 | Owen |
| 5,470,337 A | 11/1995 | Moss |
| 5,472,017 A * | 12/1995 | Kovalcheck ......... A61B 1/0052 138/103 |
| 5,474,568 A | 12/1995 | Scott et al. |
| 5,480,382 A | 1/1996 | Hammerslag et al. |
| 5,480,423 A | 1/1996 | Ravenscroft et al. |
| 5,489,295 A | 2/1996 | Piplani et al. |
| 5,522,881 A | 6/1996 | Lentz |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,591,195 A | 1/1997 | Taheri et al. |
| 5,609,627 A | 3/1997 | Giocechea et al. |
| 5,626,613 A | 5/1997 | Schmieding |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dercume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicechea et al. |
| 5,693,084 A | 12/1997 | Chuter |
| 5,693,086 A | 12/1997 | Goicechea et al. |
| 5,700,269 A | 12/1997 | Pinchuk et al. |
| 5,702,343 A | 12/1997 | Alferness |
| 5,702,365 A | 12/1997 | King |
| 5,702,408 A | 12/1997 | Wales et al. |
| 5,707,376 A | 1/1998 | Kavteledze et al. |
| 5,713,907 A | 2/1998 | Bogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,779,731 A | 7/1998 | Leavitt et al. |
| 5,782,844 A | 7/1998 | Yoon et al. |
| 5,797,933 A | 8/1998 | Snow et al. |
| 5,800,528 A | 9/1998 | Lederman et al. |
| 5,810,882 A | 9/1998 | Bolduc et al. |
| 5,814,016 A | 9/1998 | Valley et al. |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A | 11/1998 | Stein et al. |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A | 2/1999 | Whayne |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thomson et al. |
| 5,916,263 A | 6/1999 | Goicechea et al. |
| 5,938,616 A * | 8/1999 | Eaton ................. A61B 1/0052 600/446 |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |
| 5,980,548 A | 11/1999 | Evans et al. |

(56) References Cited

U.S. PATENT DOCUMENTS

| | | |
|---|---|---|
| 5,993,401 A | 11/1999 | Inbe et al. |
| 5,993,466 A | 11/1999 | Yoon |
| 5,997,556 A | 12/1999 | Tanner |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,129,685 A | 10/2000 | Howard, III |
| 6,145,509 A | 11/2000 | Tanner |
| 6,146,339 A | 11/2000 | Biagtan et al. |
| 6,152,144 A | 11/2000 | Lesh et al. |
| 6,162,168 A | 12/2000 | Schweich, Jr. et al. |
| 6,168,610 B1 | 1/2001 | Marin et al. |
| 6,174,323 B1 | 1/2001 | Biggs et al. |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 | 3/2001 | Chin et al. |
| 6,217,597 B1 | 4/2001 | Tanner |
| 6,224,540 B1 | 5/2001 | Lederman et al. |
| 6,231,561 B1 | 5/2001 | Frazier et al. |
| 6,248,118 B1 | 6/2001 | Tanner et al. |
| 6,250,974 B1 | 6/2001 | Kerek |
| 6,258,021 B1 | 7/2001 | Wilk |
| 6,258,119 B1 | 7/2001 | Hussein et al. |
| 6,270,516 B1 | 8/2001 | Tanner et al. |
| 6,273,858 B1 | 8/2001 | Fox et al. |
| 6,286,514 B1 | 9/2001 | Lemelson |
| 6,287,315 B1 | 9/2001 | Wijeratne et al. |
| 6,287,335 B1 | 9/2001 | Drasler et al. |
| 6,293,906 B1 | 9/2001 | Vanden Hoek et al. |
| 6,296,656 B1 | 10/2001 | Bolduc et al. |
| 6,302,906 B1 | 10/2001 | Goicechea et al. |
| 6,309,403 B1 | 10/2001 | Minor et al. |
| 6,319,278 B1 | 11/2001 | Quinn |
| 6,336,933 B1 | 1/2002 | Parodi |
| 6,343,605 B1 | 2/2002 | Lafontaine |
| 6,346,118 B1 | 2/2002 | Baker et al. |
| 6,352,561 B1 | 3/2002 | Leopold et al. |
| 6,361,556 B1 | 3/2002 | Chuter |
| 6,368,345 B1 | 4/2002 | Dehdashtian et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson, IV et al. |
| 6,406,420 B1 | 6/2002 | McCarthy et al. |
| 6,409,757 B1 | 6/2002 | Trout, III et al. |
| 6,416,365 B1 | 7/2002 | Iwahori |
| 6,416,522 B1 | 7/2002 | Strecker |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,461,365 B2 | 10/2002 | Bolduc et al. |
| 6,468,260 B1 | 10/2002 | Bumbalough et al. |
| 6,482,224 B1 | 11/2002 | Michler et al. |
| 6,520,974 B2 | 2/2003 | Tanner et al. |
| 6,544,253 B2 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenberg et al. |
| 6,592,593 B1 | 7/2003 | Parodi et al. |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,639,278 B2 | 10/2003 | Sumida et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B1 | 3/2004 | Lazarus |
| 6,709,442 B2 | 3/2004 | Miller et al. |
| 6,719,174 B1 | 4/2004 | Swift |
| 6,730,119 B1 | 5/2004 | Smalling |
| 6,800,081 B2 | 5/2004 | Parodi |
| 6,746,460 B2 | 6/2004 | Gannoe et al. |
| 6,878,164 B2 | 4/2005 | Kujawski et al. |
| 6,929,661 B2 | 8/2005 | Bolduc et al. |
| 6,960,217 B2 | 11/2005 | Bolduc |
| 6,984,241 B2 | 1/2006 | Lubbers et al. |
| 6,986,775 B2 | 1/2006 | Morales et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,021 B1 | 6/2006 | Wilk |
| 7,060,023 B2 | 6/2006 | French et al. |
| 7,081,086 B2 | 7/2006 | Lau et al. |
| 7,081,129 B2 | 7/2006 | Chobotov |
| 7,128,754 B2 | 10/2006 | Bolduc |
| 7,155,295 B2 | 12/2006 | Lau et al. |
| 7,179,225 B2 | 2/2007 | Shluzas et al. |
| 7,306,623 B2 | 12/2007 | Watson |
| 7,335,213 B1 | 2/2008 | Hyde et al. |
| 7,361,137 B2 | 4/2008 | Taylor et al. |
| 7,404,824 B1 | 7/2008 | Webler et al. |
| 7,422,558 B2 | 9/2008 | Lau et al. |
| 7,491,232 B2 | 2/2009 | Bolduc et al. |
| 7,544,198 B2 | 6/2009 | Parodi et al. |
| 7,591,842 B2 | 9/2009 | Parodi |
| 7,637,932 B2 | 12/2009 | Bolduc et al. |
| 7,704,269 B2 | 4/2010 | St. Goar et al. |
| 7,727,189 B2 | 6/2010 | Vantassel et al. |
| 7,753,922 B2 | 7/2010 | Starksen |
| 7,811,295 B2 | 10/2010 | Kortenbach |
| 7,823,267 B2 | 11/2010 | Bolduc et al. |
| 7,828,267 B2 | 11/2010 | Iwabuchi et al. |
| 7,828,838 B2 | 11/2010 | Bolduc et al. |
| 7,959,663 B2 | 6/2011 | Bolduc |
| 7,959,670 B2 | 6/2011 | Bolduc |
| 8,075,570 B2 | 12/2011 | Bolduc et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,685,044 B2 | 4/2014 | Bolduc et al. |
| 8,690,897 B2 | 4/2014 | Bolduc |
| 9,023,065 B2 | 5/2015 | Bolduc et al. |
| 2001/0041821 A1 | 11/2001 | Wilk |
| 2001/0047199 A1 | 11/2001 | Wijay |
| 2002/0026144 A1 | 2/2002 | Patterson |
| 2002/0029077 A1 | 3/2002 | Leopold et al. |
| 2002/0058855 A1 | 5/2002 | Cyril, Jr. et al. |
| 2002/0065485 A1 | 5/2002 | Dubois et al. |
| 2002/0082584 A1* | 6/2002 | Rosenman ........ A61M 25/0014 604/523 |
| 2002/0087169 A1 | 7/2002 | Brock et al. |
| 2002/0099432 A1 | 7/2002 | Yee |
| 2002/0133054 A1 | 9/2002 | Murphy et al. |
| 2002/0156365 A1 | 10/2002 | Tsekos |
| 2002/0156521 A1 | 10/2002 | Ryan et al. |
| 2002/0183827 A1 | 12/2002 | Derus et al. |
| 2003/0018358 A1 | 1/2003 | Saadat |
| 2003/0060674 A1 | 3/2003 | Hanson, III et al. |
| 2003/0078465 A1 | 4/2003 | Pai et al. |
| 2003/0100943 A1 | 5/2003 | Bolduc |
| 2003/0105384 A1 | 6/2003 | Sharkey et al. |
| 2003/0105519 A1 | 6/2003 | Fasol et al. |
| 2003/0130731 A1 | 7/2003 | Vidlund et al. |
| 2003/0149463 A1 | 8/2003 | Solymar et al. |
| 2003/0158570 A1 | 8/2003 | Ferrazzi |

(56) References Cited

U.S. PATENT DOCUMENTS

| | | | |
|---|---|---|---|
| 2003/0163085 A1 | 8/2003 | Tanner et al. | |
| 2003/0204249 A1 | 10/2003 | Letort | |
| 2003/0233140 A1 | 12/2003 | Hartley et al. | |
| 2004/0002731 A1 | 1/2004 | Aganon et al. | |
| 2004/0039405 A1 | 2/2004 | Petrovic et al. | |
| 2004/0044364 A1 | 3/2004 | Devries et al. | |
| 2004/0049207 A1 | 3/2004 | Goldfarb et al. | |
| 2004/0054352 A1 | 3/2004 | Adams et al. | |
| 2004/0093057 A1 | 5/2004 | Bolduc et al. | |
| 2004/0127916 A1 | 7/2004 | Bolduc et al. | |
| 2004/0138734 A1 | 7/2004 | Chobotov et al. | |
| 2004/0153143 A1 | 8/2004 | Quiachon et al. | |
| 2004/0186566 A1 | 9/2004 | Hindrichs et al. | |
| 2004/0206363 A1 | 10/2004 | McCarthy et al. | |
| 2004/0210304 A1 | 10/2004 | Seguin et al. | |
| 2004/0243170 A1 | 12/2004 | Suresh et al. | |
| 2004/0254594 A1 | 12/2004 | Alfaro | |
| 2004/0260322 A1 | 12/2004 | Rudko et al. | |
| 2004/0260383 A1 | 12/2004 | Stelter et al. | |
| 2005/0038506 A1 | 2/2005 | Webler et al. | |
| 2005/0043790 A1 | 2/2005 | Seguin et al. | |
| 2005/0049574 A1* | 3/2005 | Petrick | A61M 25/0026 604/525 |
| 2005/0070992 A1 | 3/2005 | Bolduc et al. | |
| 2005/0113906 A9 | 5/2005 | Bolduc et al. | |
| 2005/0154401 A1 | 7/2005 | Weldon et al. | |
| 2005/0177180 A1 | 8/2005 | Kaganov et al. | |
| 2005/0187613 A1 | 8/2005 | Bolduc | |
| 2005/0197716 A1 | 9/2005 | Sharkey et al. | |
| 2005/0215874 A1 | 9/2005 | Wang et al. | |
| 2005/0240258 A1 | 10/2005 | Bolduc et al. | |
| 2005/0240260 A1 | 10/2005 | Bolduc | |
| 2006/0111692 A1 | 5/2006 | Hlavka et al. | |
| 2006/0184224 A1 | 8/2006 | Angel | |
| 2006/0253186 A1 | 11/2006 | Bates | |
| 2006/0259125 A1 | 11/2006 | Peacock, III | |
| 2006/0287661 A1 | 12/2006 | Bolduc et al. | |
| 2007/0021753 A1 | 1/2007 | Bolduc et al. | |
| 2007/0021829 A1 | 1/2007 | Bolduc et al. | |
| 2007/0032860 A1 | 2/2007 | Brooks et al. | |
| 2007/0073389 A1 | 3/2007 | Bolduc et al. | |
| 2007/0083255 A1 | 4/2007 | Chiang et al. | |
| 2008/0065117 A1 | 3/2008 | Bolduc et al. | |
| 2008/0065189 A1 | 3/2008 | Bolduc | |
| 2008/0065191 A1 | 3/2008 | Bolduc et al. | |
| 2008/0097489 A1 | 4/2008 | Goldfarb et al. | |
| 2008/0132996 A1 | 6/2008 | Drasler et al. | |
| 2009/0082852 A1 | 3/2009 | Bolduc et al. | |
| 2009/0099650 A1 | 4/2009 | Bolduc et al. | |
| 2009/0112302 A1 | 4/2009 | Stafford | |
| 2009/0112303 A1 | 4/2009 | Bolduc | |
| 2009/0138072 A1 | 5/2009 | Gendreau | |
| 2010/0094400 A1 | 4/2010 | Bolduc et al. | |
| 2011/0087320 A1 | 4/2011 | Bolduc et al. | |
| 2011/0238088 A1 | 9/2011 | Bolduc et al. | |
| 2011/0276062 A1 | 11/2011 | Bolduc | |
| 2012/0065661 A1 | 3/2012 | Bolduc | |
| 2012/0316578 A1 | 12/2012 | Bolduc et al. | |
| 2014/0194902 A1 | 7/2014 | Bolduc et al. | |
| 2014/0214051 A1 | 7/2014 | Bolduc | |
| 2015/0127015 A1 | 5/2015 | Bolduc et al. | |

FOREIGN PATENT DOCUMENTS

| | | |
|---|---|---|
| AU | 2008243229 A1 | 12/2008 |
| AU | 2004287355 B2 | 6/2011 |
| AU | 2006305688 B2 | 12/2012 |
| AU | 2011253682 B9 | 1/2014 |
| AU | 2011224089 B2 | 7/2014 |
| CA | 2265131 A1 | 9/1999 |
| CA | 2344252 A1 | 3/2000 |
| CA | 2729464 A1 | 6/2003 |
| CA | 2539265 A1 | 5/2005 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2554022 A1 | 11/2012 |
| CA | 2546721 C | 9/2013 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1870951 A | 11/2006 |
| CN | 1997318 A | 7/2007 |
| CN | 101151002 A | 3/2008 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |
| CN | 101466316 B | 6/2012 |
| DE | 3333427 C2 | 5/1991 |
| DE | 69228184 T2 | 9/1999 |
| DE | 100 34 105 C1 | 4/2002 |
| DE | 10297483 T5 | 12/2004 |
| EP | 0 321 912 A1 | 6/1989 |
| EP | 0 663 184 A1 | 7/1995 |
| EP | 0 835 642 B1 | 8/2002 |
| EP | 1 369 098 A1 | 12/2003 |
| EP | 1 440 673 A1 | 7/2004 |
| EP | 1 448 117 A1 | 8/2004 |
| EP | 1 675 528 A2 | 7/2006 |
| EP | 1 725 172 A2 | 11/2006 |
| EP | 1 734 872 A1 | 12/2006 |
| EP | 1 948 080 A2 | 7/2008 |
| EP | 2 119 416 A1 | 11/2009 |
| EP | 2 349 086 A1 | 8/2011 |
| EP | 2 349 087 A1 | 8/2011 |
| FR | 2 299 548 A1 | 8/1976 |
| FR | 2865926 A1 | 8/2005 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2001526574 A | 12/2001 |
| JP | 2002526193 A | 8/2002 |
| JP | 2005046648 A | 2/2005 |
| JP | 2005510293 A | 4/2005 |
| JP | 2005510303 A | 4/2005 |
| JP | 2007508894 A | 4/2007 |
| JP | 2007508895 A | 4/2007 |
| JP | 2007523694 A | 8/2007 |
| JP | 2007535339 A | 12/2007 |
| JP | 2009512497 A | 3/2009 |
| JP | 2009512498 A | 3/2009 |
| JP | 2009512499 A | 3/2009 |
| JP | 2009078172 A | 4/2009 |
| JP | 2009095684 A | 5/2009 |
| JP | 2009106763 A | 5/2009 |
| JP | 2009106768 A | 5/2009 |
| JP | 2009106775 A | 5/2009 |
| JP | 2009112827 A | 5/2009 |
| JP | 2009519046 A | 5/2009 |
| JP | 4405262 B2 | 1/2010 |
| JP | 10506026 A | 2/2010 |
| JP | 2010051786 A | 3/2010 |
| JP | 4465359 B2 | 5/2010 |
| JP | 2011062570 A | 3/2011 |
| JP | 4699445 B2 | 6/2011 |
| WO | WO-93/00868 A1 | 1/1993 |
| WO | WO-95/21592 A1 | 8/1995 |
| WO | WO-96/03925 A1 | 2/1996 |
| WO | WO-97/03616 A1 | 2/1997 |
| WO | WO-1997003616 A1 | 2/1997 |

(56) References Cited

FOREIGN PATENT DOCUMENTS

| WO | 9712562 A1 | 4/1997 |
|---|---|---|
| WO | 9717039 A1 | 5/1997 |
| WO | 9717913 A1 | 5/1997 |
| WO | 9811814 A2 | 3/1998 |
| WO | WO-98/53761 A1 | 12/1998 |
| WO | 9930637 A1 | 6/1999 |
| WO | 9933402 A1 | 7/1999 |
| WO | 9933402 A9 | 9/1999 |
| WO | WO-99/53845 A1 | 10/1999 |
| WO | WO-1999053845 A1 | 10/1999 |
| WO | 00/16701 A1 | 3/2000 |
| WO | 00/35350 A1 | 6/2000 |
| WO | 00/64357 A1 | 11/2000 |
| WO | 01/60432 A1 | 8/2001 |
| WO | WO-03032870 A1 | 4/2003 |
| WO | 03/045283 A1 | 6/2003 |
| WO | 03/045467 A2 | 6/2003 |
| WO | 03/079935 A2 | 10/2003 |
| WO | WO-2004008975 A1 | 1/2004 |
| WO | WO-2004021872 A2 | 3/2004 |
| WO | WO-2005/032333 A2 | 4/2005 |
| WO | WO-2005/032333 A3 | 4/2005 |
| WO | WO-2005037076 A2 | 4/2005 |
| WO | WO-2005/044073 A2 | 5/2005 |
| WO | WO-2005/044073 A3 | 5/2005 |
| WO | WO-2005044147 A1 | 5/2005 |
| WO | WO-2005044148 A1 | 5/2005 |
| WO | WO-2005067660 A2 | 7/2005 |
| WO | WO-2005/081936 A2 | 9/2005 |
| WO | WO-2005/081936 A3 | 9/2005 |
| WO | WO-2005102181 A1 | 11/2005 |
| WO | WO-2007/046953 A2 | 4/2007 |
| WO | WO-2007/046953 A3 | 4/2007 |
| WO | WO-2007/046954 A2 | 4/2007 |
| WO | WO-2007/046954 A3 | 4/2007 |
| WO | WO-2007/046955 A2 | 4/2007 |
| WO | WO-2007/046955 A3 | 4/2007 |
| WO | WO-2007/047023 A2 | 4/2007 |
| WO | WO-2007/047023 A3 | 4/2007 |
| WO | WO-2005067660 A3 | 4/2007 |
| WO | WO-2007053233 A2 | 5/2007 |
| WO | WO-20070532333 A3 | 1/2008 |
| WO | WO-2010004856 A1 | 1/2010 |
| WO | WO-2010/044851 A1 | 4/2010 |
| WO | WO-2010/044856 A1 | 4/2010 |
| WO | WO-2010044854 A1 | 4/2010 |
| WO | WO-2010044855 A1 | 4/2010 |

OTHER PUBLICATIONS

"Australian Application Serial No. 2002353807, First Examiner Report dated Nov. 16, 2006", 2 pgs.
"Australian Application Serial No. 2004277897, First Examiner Report dated Oct. 14, 2009", 2 pgs.
"Australian Application Serial No. 2004277897, Response filed Jul. 14, 2011 to First Examiner Report dated Oct. 14, 2009", 9 pgs.
"Australian Application Serial No. 2004287354, Office Action dated Oct. 13, 2009", 2 pgs.
"Australian Application Serial No. 2004287355, European Search report dated Oct. 14, 2009", 6 pgs.
"Australian Application Serial No. 2004287355, Office Action dated May 11, 2009", 2 pgs.
"Australian Application Serial No. 2005204615, Office Action dated Jan. 20, 2010", 4 pgs.
"Australian Application Serial No. 2005235108, Office Action dated Feb. 26, 2010", 3 pgs.
"Australian Application Serial No. 2006302908, Office Action dated Mar. 4, 2011", 8 pgs.
"Australian Application Serial No. 2006305688, First Examiner Report dated Mar. 10, 2011", 3 pgs.
"Australian Application Serial No. 2006305688, Response filed Oct. 22, 2012 to First Examiner Report dated Mar. 10, 2011", 16 pgs.
"Australian Application Serial No. 2006305689, Office Action dated Sep. 5, 2011", 3 pgs.
"Australian Application Serial No. 2006309241, Office Action dated Mar. 4, 2011", 6 pgs.
"Australian Application Serial No. 2008243229, First Examiner Report dated Apr. 13, 2010", 2 pgs.
"Australian Application Serial No. 2008243229, Response filed May 13, 2011 to Office Action dated Apr. 13, 2010", 15 pgs.
"Australian Application Serial No. 2011224089, First Examiners Report dated Mar. 27, 2013", 3 pgs.
"Australian Application Serial No. 2011224089, Response filed Mar. 21, 2014 to First Examiners Report dated Mar. 27, 2013", 74 pgs.
"Canadian Application Serial No. 2,464,900, Office Action dated Sep. 29, 2009", 3 pgs.
"Canadian Application Serial No. 2,539,585, Office Action dated Aug. 31, 2010", 2 pgs.
"Canadian Application Serial No. 2,539,585, Office Action dated Sep. 19, 2012", 2 pgs.
"Canadian Application Serial No. 2,546,681, Office Action dated Feb. 25, 2011", 3 pgs.
"Canadian Application Serial No. 2,546,721, Office Action dated Feb. 25, 2011", 3 pgs.
"Canadian Application Serial No. 2,546,721, Office Action dated Aug. 31, 2010", 2 pgs.
"Canadian Application Serial No. 2,546,721, Response filed Aug. 1, 2012 to Office Action dated Feb. 25, 2011", 9 pgs.
"Canadian Application Serial No. 2,551,685, Office Action dated Jan. 17, 2011", 3 pgs.
"Canadian Application Serial No. 2,554,022, Office Action dated Jun. 22, 2011", 3 pgs.
"Canadian Application Serial No. 2,554,022, Office Action dated Aug. 31, 2010", 2 pgs.
"Canadian Application Serial No. 2,558,317, Office Action dated Aug. 31, 2010", 2 pgs.
"Canadian Application Serial No. 2,558,317, Office Action dated Sep. 28, 2011", 3 pgs.
"Canadian Application Serial No. 2,626,403, Office Action dated Apr. 2, 2013", 3 pgs.
"Canadian Application Serial No. 2,626,403, Response filed Feb. 12, 2014 to Office Action dated Apr. 2, 2013", 20 pgs.
"Canadian Application Serial No. 2,626,403, Voluntary Amendment filed Feb. 25, 2014", 6 pgs.
"Chinese Application Serial No. 02823581.9, Office Action dated Mar. 1, 2006", 7 pgs.
"Chinese Application Serial No. 02823581.9, Office Action dated Apr. 18, 2008", 6 pgs.
"Chinese Application Serial No. 02823581.9, Office Action dated Aug. 8, 2007", 4 pgs.
"Chinese Application Serial No. 02823581.9, Office Action dated Nov. 17, 2006", 7 pgs.
"Chinese Application Serial No. 02823581.9, Response filed Jan. 31, 2007 to Office Action dated Nov. 17, 2006", 8 pgs.
"Chinese Application Serial No. 02823581.9, Response filed Apr. 7, 2006 to Office Action dated Mar. 1, 2006", 4 pgs.
"Chinese Application Serial No. 02823581.9, Response filed May 19, 2008 to Office Action dated Apr. 18, 2008", 38 pgs.
"Chinese Application Serial No. 02823581.9, Response filed Dec. 3, 2007 to Office Action dated Aug. 8, 2007", 6 pgs.
"Chinese Application Serial No. 200480027649.7, Office Action dated Jun. 23, 2008", w/English Translation, 5 pgs.
"Chinese Application Serial No. 200480027649.7, Office Action dated Sep. 4, 2009", w/English Translation, 18 pgs.
"Chinese Application Serial No. 200480027649.7, Office Action dated Dec. 24, 2010", w/English translation, 6 pgs.
"Chinese Application Serial No. 200480027649.7, Response filed Jan. 19, 2010 to Office Action dated Sep. 4, 2009", 5 pgs.
"Chinese Application Serial No. 200480027649.7, Response filed Mar. 8, 2011 to Office Action dated Dec. 24, 2010", w/ English translation, 7 pgs.
"Chinese Application Serial No. 200480031226.2, Office Action dated Jan. 23, 2009", 9 pgs.

(56) References Cited

OTHER PUBLICATIONS

"Chinese Application Serial No. 200480031226.2, Office Action dated Apr. 27, 2010", 7 pgs.
"Chinese Application Serial No. 200480031226.2, Office Action dated Dec. 21, 2010", 10 pgs.
"U.S. Appl. No. 10/752,435, Response filed Sep. 19, 2008 to Non Final Office Action dated Mar. 18, 2008", 7 pgs.
"U.S. Appl. No. 10/786,465, Applicant's Summary of Examiner Interview filed Jun. 6, 2012", 2 pgs.
"European Application Serial No. 06802573.3, Extended European Search Report dated Feb. 15, 2012", 6 pgs.
"U.S. Appl. No. 10/786,465, Examiner Interview Summary dated Mar. 3, 2008", 2 pgs.
"U.S. Appl. No. 10/786,465, Examiner Interview Summary dated Apr. 26, 2011", 3 pgs.
"U.S. Appl. No. 10/786,465, Final Office Action dated Jan. 21, 2009", 8 pgs.
"U.S. Appl. No. 10/786,465, Non Final Office Action dated Mar. 26, 2010", 8 pgs.
"U.S. Appl. No. 10/786,465, Non Final Office Action dated Jul. 23, 2007", 7 pgs.
"U.S. Appl. No. 10/786,465, Notice of Allowance dated Mar. 14, 2012", 11 pgs.
"U.S. Appl. No. 10/786,465, Preliminary Amendment filed May 16, 2005", 3 pgs.
"U.S. Appl. No. 10/786,465, Response filed Jan. 25, 2008 to Non Final Office Action dated Jul. 23, 2007", 8 pgs.
"U.S. Appl. No. 10/786,465, Response filed Apr. 9, 2007 to Restriction Requirement dated Dec. 8, 2006", 4 pgs.
"U.S. Appl. No. 10/786,465, Response filed Apr. 26, 2011 to Non Final Office Action dated Mar. 26, 2010", 14 pgs.
"U.S. Appl. No. 10/786,465, Response filed Jul. 22, 2009 to Final Office Action dated Jan. 21, 2009", 5 pgs.
"U.S. Appl. No. 10/786,465, Response filed Sep. 19, 2008 to Restriction Requirement dated Jul. 24, 2008", 4 pgs.
"U.S. Appl. No. 10/786,465, Restriction Requirement dated Jul. 24, 2008", 5 pgs.
"U.S. Appl. No. 10/786,465, Restriction Requirement dated Dec. 8, 2006", 6 pgs.
"U.S. Appl. No. 10/786,465, Supplemental Amendment filed Mar. 18, 2008", 8 pgs.
"U.S. Appl. No. 10/786,465, Supplemental Notice of Allowability dated May 8, 2012", 6 pgs.
"U.S. Appl. No. 10/808,216, Preliminary Amendment filed Jun. 15, 2005", 3 pgs.
"U.S. Appl. No. 11/166,411, 312 Amendment filed Nov. 23, 2011", 3 pgs.
"U.S. Appl. No. 11/166,411, Final Office Action dated Dec. 3, 2009", 5 pgs.
"U.S. Appl. No. 11/166,411, Non Final Office Action dated May 5, 2009", 8 pgs.
"U.S. Appl. No. 11/166,411, Preliminary Amendment Filed Oct. 2, 2006", 5 pgs.
"U.S. Appl. No. 11/166,411, PTO Response to 312 Communication dated Dec. 13, 2011", 2 pgs.
"U.S. Appl. No. 11/166,411, Response filed Jan. 12, 2009 to Restriction Requirement dated Jul. 15, 2008", 2 pgs.
"U.S. Appl. No. 11/166,411, Response filed Jun. 7, 2010 to Final Office Action dated Dec. 3, 2009", 5 pgs.
"U.S. Appl. No. 11/166,411, Response filed Nov. 9, 2009 to Non Final Office Action dated May 5, 2009", 8 pgs.
"U.S. Appl. No. 11/166,411, Restriction Requirement dated Jul. 15, 2008", 5 pgs.
"U.S. Appl. No. 11/166,411, Supplemental Preliminary Amendment filed Oct. 30, 2007", 7 pgs.
"U.S. Appl. No. 11/166,428, Final Office Action dated Jan. 12, 2009", 10 pgs.
"U.S. Appl. No. 11/166,428, Final Office Action dated Mar. 16, 2010", 8 pgs.
"U.S. Appl. No. 11/166,428, Non Final Office Action dated May 14, 2008", 6 pgs.
"U.S. Appl. No. 11/166,428, Non Final Office Action dated Jun. 16, 2009", 10 pgs.
"U.S. Appl. No. 11/166,428, Response filed May 12, 2009 to Final Office Action dated Jan. 12, 2009", 6 pgs.
"U.S. Appl. No. 11/166,428, Response filed Nov. 17, 2008 to Non Final Office Action dated May 14, 2008", 6 pgs.
"U.S. Appl. No. 11/166,428, Response filed Dec. 22, 2009 to Non Final Office Action dated Dec. 16, 2009", 8 pgs.
"U.S. Appl. No. 11/254,444, Notice of Allowance dated Mar. 9, 2010", 7 pgs.
"U.S. Appl. No. 11/254,444, Notice of Allowance dated Apr. 5, 2010", 4 pgs.
"U.S. Appl. No. 11/254,444, Notice of Allowance dated Jun. 29, 2010", 6 pgs.
"U.S. Appl. No. 11/254,444, Preliminary Amendment filed Oct. 20, 2005".
"U.S. Appl. No. 11/254,444, Preliminary Amendment filed Nov. 15, 2005", 8 pgs.
"U.S. Appl. No. 11/254,444, Response filed Dec. 18, 2009 to Restriction Requirement dated Jun. 19, 2009", 2 pgs.
"U.S. Appl. No. 11/254,444, Restriction Requirement dated Jun. 19, 2009", 6 pgs.
"U.S. Appl. No. 11/254,950, Non Final Office Action dated Mar. 30, 2009", 6 pgs.
"U.S. Appl. No. 11/254,950, Notice of Allowance dated Feb. 26, 2010", 4 pgs.
"U.S. Appl. No. 11/254,950, Notice of Allowance dated Jun. 22, 2010", 4 pgs.
"U.S. Appl. No. 11/254,950, Preliminary Amendment filed Nov. 18, 2005", 4 pgs.
"U.S. Appl. No. 11/254,950, Response filed Jan. 5, 2009 to Restriction Requirement dated Jul. 9, 2008", 7 pgs.
"U.S. Appl. No. 11/254,950, Response filed Oct. 5, 2009 to Non Final Office Action dated Mar. 30, 2009", 5 pgs.
Written Opinion dated Dec. 18, 2009, for PCT/US2009/005609, filed Oct. 14, 2009, 6 pages.
"International Application Serial No. PCT/US2005/005453, Written Opinion dated Aug. 30, 2005", 3 pgs.
"U.S. Appl. No. 12/653,219, Non Final Office Action dated May 30, 2012", 16 pgs.
"U.S. Appl. No. 12/917,842, Non Final Office Action dated Nov. 13, 2012", 6 pgs.
"U.S. Appl. No. 12/917,842, Notice of Allowance dated May 20, 2013", 8 pgs.
"U.S. Appl. No. 12/917,842, Notice of Allowance dated Aug. 27, 2013", 6 pgs.
"U.S. Appl. No. 12/917,842, Notice of Allowance dated Dec. 2, 2013", 7 pgs.
"U.S. Appl. No. 12/917,842, Response filed Apr. 15, 2013 to Non Final Office Action dated Nov. 13, 2012", 9 pgs.
"U.S. Appl. No. 12/917,842, Response filed Oct. 15, 2012 to Restriction Requirement dated Sep. 14, 2012", 2 pgs.
"U.S. Appl. No. 12/917,842, Restriction Requirement dated Sep. 14, 2012", 5 pgs.
"U.S. Appl. No. 12/942,232, Advisory Action dated Aug. 7, 2014", 3 pgs.
"U.S. Appl. No. 12/942,232, Final Office Action dated May 22, 2014", 17 pgs.
"U.S. Appl. No. 12/942,232, Non Final Office Action dated Oct. 9, 2013", 13 pgs.
"U.S. Appl. No. 12/942,232, Response filed Jan. 9, 2014 to Non Final Office Action dated Oct. 9, 2013", 11 pgs.
"U.S. Appl. No. 12/942,232, Response filed Jul. 21, 2014 to Final Office Action dated May 22, 2014", 11 pgs.
"U.S. Appl. No. 13/157,242, Advisory Action dated Jul. 30, 2013", 3 pgs.
"U.S. Appl. No. 13/157,242, Final Office Action dated May 16, 2013", 7 pgs.
"U.S. Appl. No. 13/157,242, Non Final Office Action dated Jun. 18, 2012", 9 pgs.

(56) References Cited

OTHER PUBLICATIONS

"U.S. Appl. No. 13/157,242, Non Final Office Action dated Oct. 31, 2013", 6 pgs.
"U.S. Appl. No. 13/157,242, Notice of Allowance dated Jan. 14, 2015", 8 pgs.
"U.S. Appl. No. 13/157,242, Notice of Allowance dated Feb. 26, 2014", 8 pgs.
"U.S. Appl. No. 13/157,242, Notice of Allowance dated May 9, 2014", 8 pgs.
"U.S. Appl. No. 13/157,242, Notice of Allowance dated Aug. 21, 2014", 8 pgs.
"U.S. Appl. No. 13/157,242, Preliminary Amendment filed Jun. 9, 2011", 7 pgs.
"U.S. Appl. No. 13/157,242, Response filed Jan. 28, 2014 to Non Final Office Action dated Oct. 31, 2013", 11 pgs.
"U.S. Appl. No. 13/157,242, Response filed Jun. 1, 2012 to Restriction Requirement dated May 1, 2012", 3 pgs.
"U.S. Appl. No. 13/157,242, Response filed Jul. 16, 2013 to Final Office Action dated May 16, 2013", 9 pgs.
"U.S. Appl. No. 13/157,242, Response filed Dec. 18, 2012 to Non Final Office Action dated Jun. 18, 2012", 11 pgs.
"U.S. Appl. No. 13/157,242, Restriction Requirement dated May 1, 2012", 6 pgs.
"U.S. Appl. No. 13/162,384, Advisory Action dated Nov. 15, 2013", 3 pgs.
"U.S. Appl. No. 13/162,384, Examiner Interview Summary dated Oct. 22, 2014", 3 pgs.
"U.S. Appl. No. 13/162,384, Examiner Interview Summary dated Feb. 24, 2015", 1 pg.
"U.S. Appl. No. 13/162,384, Final Office Action dated Aug. 27, 2013", 14 pgs.
"U.S. Appl. No. 13/162,384, Non Final Office Action dated Feb. 24, 2015", 14 pgs.
"U.S. Appl. No. 13/162,384, Non Final Office Action dated Mar. 28, 2013", 8 pgs.
"U.S. Appl. No. 13/162,384, Non Final Office Action dated Jul. 21, 2014", 15 pgs.
"U.S. Appl. No. 13/162,384, Preliminary Amendment filed Jun. 16, 2011", 7 pgs.
"U.S. Appl. No. 13/162,384, Response filed Jun. 27, 2013", 9 pgs.
"U.S. Appl. No. 13/162,384, Response filed Oct. 18, 2013 to Final Office Action dated Aug. 27, 2013", 5 pgs.
"U.S. Appl. No. 13/162,384, Response filed Oct. 20, 2014 to Non Final Office Action dated Jul. 21, 2014", 12 pgs.
"U.S. Appl. No. 13/495,836, Non Final Office Action dated Aug. 5, 2013", 7 pgs.
"U.S. Appl. No. 13/495,836, Non Final Office Action dated Dec. 26, 2012", 9 pgs.
"U.S. Appl. No. 13/495,836, Notice of Allowance dated Dec. 4, 2013", 9 pgs.
"U.S. Appl. No. 13/495,836, Preliminary Amendment filed Jun. 13, 2012", 8 pgs.
"U.S. Appl. No. 13/495,836, Response filed Mar. 26, 2013 to Non Final Office Action dated Dec. 26, 2012", 9 pgs.
"U.S. Appl. No. 13/495,836, Response filed Nov. 5, 2013 to Non Final Office Action dated Aug. 5, 2013", 8 pgs.
"U.S. Appl. No. 14/210,683, Preliminary Amendment dated Mar. 24, 2014", 7 pgs.
"U.S. Appl. No. 14/230,469, Non Final Office Action dated May 7, 2015", 8 pgs.
"U.S. Appl. No. 14/595,928, Preliminary Amendment filed Jan. 14, 2015", 8 pgs.
"Australian Application Serial No. 2011253682, Office Action dated Sep. 27, 2012", 4 pgs.
"Australian Application Serial No. 2011253682, Response filed Jul. 17, 2013 to Office Action dated Sep. 27, 2012", 19 pgs.
"Australian Application Serial No. 2002351188, Office Action dated Mar. 30, 2007", 1 pg.
"Chinese Application Serial No. 200480031226.2, Response filed Feb. 25, 2011 to Office Action dated Dec. 21, 2010", 18 pgs.
"Chinese Application Serial No. 200480031226.2, Response filed May 22, 2009 to Office Action dated Jan. 23, 2009", 5 pgs.
"Chinese Application Serial No. 200480031226.2, Response filed Jul. 12, 2010 to Office Action dated Apr. 27, 2010", Chinese only, 5 pgs.
"Chinese Application Serial No. 200580002026.9, Office Action dated Jun. 19, 2009", 12 pgs.
"Chinese Application Serial No. 200580002026.9, Response filed Jan. 4, 2010 to Office Action dated Jun. 19, 2009", 10 pgs.
"Chinese Application Serial No. 200580006169.7, Office Action dated Mar. 1, 2010", w/English translation, 12 pgs.
"Chinese Application Serial No. 200580006169.7, Response filed Jul. 14, 2010 to Office Action dated Mar. 1, 2010", w/English translation, 32 pgs.
"Chinese Application Serial No. 200580009570.6, Office Action dated May 9, 2008".
"Chinese Application Serial No. 200580009570.6, Response filed Nov. 21, 2008 to Office Action dated May 9, 2008", 7 pgs.
"Chinese Application Serial No. 200680034052.4, Office Action dated May 11, 2010", w/English translation, 7 pgs.
"Chinese Application Serial No. 200680034052.4, Office Action dated Aug. 14, 2009", w/English translation, 13 pgs.
"Chinese Application Serial No. 200680034052.4, Response filed Mar. 1, 2010 to Office Action dated Aug. 14, 2009", 4 pgs.
"Chinese Application Serial No. 200680034052.4, Response filed Sep. 26, 2010 to Office Action dated May 11, 2010", 5 pgs.
"Chinese Application Serial No. 200680038882.4, Office Action dated May 11, 2010", 18 pgs.
"Chinese Application Serial No. 200680046854.7, Office Action dated Apr. 14, 2010", 18 pgs.
"Chinese Application Serial No. 200680046854.7, Response filed Sep. 26, 2010 to Office Action dated Apr. 14, 2010", 10 pgs.
"Chinese Application Serial No. 200680047552.1, Office Action dated Jun. 4, 2010", 7 pgs.
"Chinese Application Serial No. 200680047552.1, Response filed Dec. 20, 2010 to Office Action dated Jun. 4, 2010", 10 pgs.
"Chinese Application Serial No. 200810210922.X, Office Action dated Jan. 19, 2012", 6 pgs.
"Chinese Application Serial No. 200810210922.X, Office Action dated Apr. 2, 2010", 4 pgs.
"Chinese Application Serial No. 200810210922.X, Office Action dated Aug. 23, 2011", 6 pgs.
"Chinese Application Serial No. 200810210922.X, Response filed Jun. 1, 2012 to Office Action dated Jan. 19, 2012", 5 pgs.
"Chinese Application Serial No. 200810210922.X, Response filed Aug. 12, 2010 to Office Action dated Apr. 2, 2010", 10 pgs.
"Chinese Application Serial No. 200910139527.1, Office Action dated Jul. 12, 2010", w/English translation, 9 pgs.
"Chinese Application Serial No. 200910139527.1, Response filed Nov. 28, 2011 to Office Action dated Jul. 12, 2010", 9 pgs.
"European Application Serial No. 02789196.9, European Search Report dated Aug. 14, 2009", 5 pgs.
"European Application Serial No. 02789196.9, Office Action dated Feb. 6, 2012", 4 pgs.
"European Application Serial No. 02789196.9, Office Action dated Mar. 7, 2012", 3 pgs.
"European Application Serial No. 02789196.9, Office Action dated Apr. 19, 2010", 4 pgs.
"European Application Serial No. 02789196.9, Office Action dated Jul. 14, 2011", 3 pgs.
"European Application Serial No. 02789196.9, Response filed Jan. 18, 2012 to Office Action dated Jul. 14, 2011", 19 pgs.
"European Application Serial No. 02789196.9, Response filed Feb. 16, 2012 to Office Action dated Feb. 6, 2012", 9 pgs.
"European Application Serial No. 02789196.9, Response filed Apr. 5, 2012 to Office Action dated Mar. 7, 2012", 5 pgs.
"European Application Serial No. 02789196.9, Response filed Oct. 25, 2010 to Office Action dated Apr. 19, 2010", 16 pgs.
"European Application Serial No. 04788653.6, European Search Report dated Aug. 6, 2014", 3 pgs.
"European Application Serial No. 04788653.6, Examination Notification Art. 94(3) dated Mar. 3, 2015", 4 pgs.

(56) References Cited

OTHER PUBLICATIONS

"European Application Serial No. 04788653.6, Office Action dated May 19, 2006", 2 pgs.
"European Application Serial No. 04788653.6, Response filed Oct. 21, 2014 to European Search Report dated Aug. 6, 2014", 4 pgs.
"European Application Serial No. 05704902.5, European Search Report dated Aug. 29, 2011", 3 pgs.
"European Application Serial No. 05713941.2, European Search Report dated Apr. 10, 2014", 6 pgs.
"European Application Serial No. 05713941.2, Examination Notification Art. 94(3) dated Jun. 5, 2014", 7 pgs.
"European Application Serial No. 05713941.2, Office Action dated Dec. 13, 2007", 2 pgs.
"European Application Serial No. 05713941.2, Response filed Dec. 22, 2014 to Examination Notification Art. 94(3) dated Jun. 5, 2014", 15 pgs.
"European Application Serial No. 05723408.0, Examination Notification Art. 94(3) dated Jul. 10, 2014", 6 pgs.
"European Application Serial No. 05723408.0, Response filed Jan. 19, 2015 to Examination Notification Art. 94(3) dated Jul. 10, 2014", 16 pgs.
"European Application Serial No. 06802573.3, Office Action dated Mar. 5, 2012", 1 pg.
"European Application Serial No. 06802573.3, Office Action dated May 28, 2008", 2 pgs.
"European Application Serial. No. 06802573.3, Response filed Sep. 3, 2012 to Office Action dated Mar. 5, 2012", 15 pgs.
"European Application Serial. No. 06802578.2, European Search Report dated Mar. 7, 2013", 10 pgs.
"European Application Serial. No. 06802580.8, Extended European Search Report dated Sep. 24, 2013", 8 pgs.
"U.S. Appl. No. 11/254,950, Restriction Requirement dated Jul. 9, 2008", 9 pgs.
"U.S. Appl. No. 11/255,116, Preliminary Amendment filed Nov. 18, 2005", 4 pgs.
"U.S. Appl. No. 11/255,116, Response filed May 20, 2009 to Restriction Requirement dated Mar. 18, 2009", 4 pgs.
"U.S. Appl. No. 11/255,116, Response filed Nov. 17, 2008 to Non Final Office Action dated May 24, 2008", 7 pgs.
"U.S. Appl. No. 11/255,116, Restriction Requirement dated Mar. 18, 2009", 7 pgs.
"U.S. Appl. No. 11/365,056, Final Office Action dated Dec. 9, 2010", 13 pgs.
"U.S. Appl. No. 11/365,056, Non Final Office Action dated Mar. 23, 2010", 11 pgs.
"U.S. Appl. No. 11/365,056, Response filed Sep. 28, 2010 to Non Final Office Action dated Mar. 23, 2010", 5 pgs.
"U.S. Appl. No. 11/365,056, Response filed Dec. 10, 2009 to Restriction Requirement dated Jun. 10, 2009", 44 pgs.
"U.S. Appl. No. 11/365,056, Restriction Requirement dated Jun. 20, 2009", 5 pgs.
"U.S. Appl. No. 11/488,305, Advisory Action dated Jun. 7, 2013", 3 pgs.
"U.S. Appl. No. 11/488,305, Final Office Action dated Mar. 6, 2013", 9 pgs.
"U.S. Appl. No. 11/488,305, Final Office Action dated Aug. 14, 2014", 11 pgs.
"U.S. Appl. No. 11/488,305, Non Final Office Action dated Jan. 29, 2014", 10 pgs.
"U.S. Appl. No. 11/488,305, Non Final Office Action dated Sep. 14, 2012", 9 pgs.
"U.S. Appl. No. 11/488,305, Response filed Feb. 1, 2011 to Non Final Office Action dated Sep. 1, 2010", 12 pgs.
"U.S. Appl. No. 11/488,305, Response filed Feb. 13, 2013 to Non Final Office Action dated Sep. 14, 2012", 10 pgs.
"U.S. Appl. No. 11/488,305, Response filed Apr. 26, 2012 to Final Office Action dated Oct. 31, 2011", 12 pgs.
"U.S. Appl. No. 11/488,305, Response filed Apr. 29, 2014 to Non Office Action dated Jan. 29, 2014", 9 pgs.
"U.S. Appl. No. 11/488,305, Response filed May 3, 2013 to Final Office Action dated Mar. 6, 2013", 11 pgs.
"U.S. Appl. No. 11/488,305, Response filed Jul. 2, 2010 to Restriction Requirement dated Jan. 5, 2010", 8 pgs.
"U.S. Appl. No. 11/488,305, Response filed Oct. 13, 2011 to Final Office Action dated Apr. 13, 2011", 11 pgs.
"U.S. Appl. No. 11/488,305, Restriction Requirement dated Jan. 5, 2010", 6 pgs.
"U.S. Appl. No. 11/540,427, Appeal Brief filed Aug. 26, 2010", 26 pgs.
"U.S. Appl. No. 11/540,427, Notice of Allowance dated Apr. 11, 2011", 8 pgs.
"U.S. Appl. No. 11/540,427, Preliminary Amendment filed Oct. 3, 2007", 5 pgs.
"U.S. Appl. No. 11/540,427, Response filed Apr. 10, 2009 to Non Final Office Action dated Oct. 6, 2008", 6 pgs.
"U.S. Appl. No. 11/540,428, Non Final Office Action dated Nov. 12, 2010", 8 pgs.
"U.S. Appl. No. 11/540,428, Response filed May 12, 2011 to Non Final Office Action dated Nov. 12, 2010", 12 pgs.
"U.S. Appl. No. 11/540,428, Response filed Oct. 1, 2010 to Restriction Requirement dated Mar. 29, 2010", 6 pgs.
"U.S. Appl. No. 11/540,428, Restriction Requirement dated Mar. 29, 2010", 9 pgs.
"U.S. Appl. No. 11/580,584, Appeal Brief filed Nov. 15, 2010", 11 pgs.
"U.S. Appl. No. 11/580,584, Final Office Action dated Jan. 22, 2009", 9 pgs.
"U.S. Appl. No. 11/580,584, Final Office Action dated Oct. 16, 2009", 8 pgs.
"U.S. Appl. No. 11/580,584, Non Final Office Action dated Apr. 18, 2008", 6 pgs.
"U.S. Appl. No. 11/580,584, Notice of Allowance dated Feb. 4, 2011", 7 pgs.
"U.S. Appl. No. 11/580,584, Response filed Jul. 22, 2009 to Final Office Action dated Jan. 22, 2009", 6 pgs.
"U.S. Appl. No. 11/580,584, Response filed Oct. 20, 2008 to Non Final Office Action dated Apr. 18, 2008", 5 pgs.
"U.S. Appl. No. 11/978,752, Final Office Action dated Dec. 22, 2010", 6 pgs.
"U.S. Appl. No. 11/978,752, Non Final Office Action dated May 20, 2010", 6 pgs.
"U.S. Appl. No. 11/978,752, Response filed May 10, 2010 to Restriction Requirement dated Nov. 6, 2009", 4 pgs.
"U.S. Appl. No. 11/978,752, Response filed Jun. 22, 2011 to Final Office Action dated Dec. 22, 2010", 6 pgs.
"U.S. Appl. No. 11/978,752, Response filed Nov. 5, 2010 to Non Final Office Action dated May 20, 2010", 4 pgs.
"U.S. Appl. No. 11/978,752, Restriction Requirement dated Nov. 6, 2009", 7 pgs.
"U.S. Appl. No. 11/978,753, Response filed Mar. 3, 2011 to Non Final Office Action dated Sep. 3, 2010", 9 pgs.
"U.S. Appl. No. 11/981,112, Advisory Action dated Jan. 31, 2014", 3 pgs.
"U.S. Appl. No. 11/981,112, Examiner Interview Summary dated Jul. 3, 2014", 3 pgs.
"U.S. Appl. No. 11/981,112, Final Office Action dated Apr. 29, 2010", 9 pgs.
"U.S. Appl. No. 11/981,112, Final Office Action dated Oct. 8. 2013", 9 pgs.
"U.S. Appl. No. 11/981,112, Final Office Action dated Oct. 24, 2014", 7 pgs.
"U.S. Appl. No. 11/981,112, Non Final Office Action dated Feb. 28, 2014", 9 pgs.
"U.S. Appl. No. 11/981,112, Non Final Office Action dated Jul. 8, 2009", 11 pgs.
"U.S. Appl. No. 11/981,112, Response filed Jan. 6, 2010 to Non Final Office Action dated Jul. 8, 2009", 7 pgs.
"U.S. Appl. No. 11/981,112, Response file dJan. 8, 2014 to Final Office Action dated Oct. 8, 2013", 11 pgs.
"U.S. Appl. No. 11/981,112, Response filed Jan. 12, 2014 to Final Office Action dated Oct. 24, 2014", 9 pgs.

(56) References Cited

OTHER PUBLICATIONS

"U.S. Appl. No. 11/981,112, Response filed Jun. 27, 2014 to non Final Office Action dated Feb. 28, 2014", 11 pgs.
"U.S. Appl. No. 11/981,112, Response filed Nov. 1, 2010 to Final Office Action dated Apr. 29, 2010", 7 pgs.
"U.S. Appl. No. 12/288,031, Advisory Action dated Jul. 7, 2014", 4 pgs.
"U.S. Appl. No. 12/288,031, Non Final Office action dated May 10, 2012", 7 pgs.
"U.S. Appl. No. 12/288,031, Response filed Jun. 5, 2014 to Final Office Action dated Mar. 12, 2014", 15 pgs.
"U.S. Appl. No. 12/288,031, Response filed Sep. 10, 2014 to Advisory Action dated Jul. 7, 2014", 16 pgs.
"U.S. Appl. No. 12/288,031, Advisory Action dated Apr. 12, 2013", 3 pgs.
"U.S. Appl. No. 12/288,031, Final Office Action dated Jan. 3, 2012", 9 pgs.
"U.S. Appl. No. 12/288,031, Final Office Action dated Mar. 12, 2014", 14 pgs.
"U.S. Appl. No. 12/288,031, Non Final Office Action dated Feb. 17, 2015", 17 pgs.
"U.S. Appl. No. 12/288,031, Non Final Office Action dated Jul. 15, 2013", 9 pgs.
"U.S. Appl. No. 12/288,031, Response filed Mar. 25, 2013 to Final Office Action dated Jan. 3, 2013", 11 pgs.
"U.S. Appl. No. 12/288,031, Response filed Apr. 4, 2012 to Restriction Requirement dated Nov. 4, 2011", 3 pgs.
"U.S. Appl. No. 12/288,031, Response filed Oct. 10, 2012 to Non Final Office Action dated May 10, 2012", 11 pgs.
"U.S. Appl. No. 12/288,031, Response filed Nov. 15, 2013 to Non Final Office Action dated Jul. 15, 2013", 11 pgs.
"U.S. Appl. No. 12/288,031, Restriction Requirement dated Nov. 4, 2011", 9 pgs.
"U.S. Appl. No. 12/288,032, Restriction Requirement dated Nov. 4, 2011", 9 pgs.
"U.S. Appl. No. 12/288,034, Advisory Action dated Feb. 25, 2014", 3 pgs.
"U.S. Appl. No. 12/288,034, Final Office Action dated Nov. 4, 2013", 8 pgs.
"U.S. Appl. No. 12/288,034, Final Office Action dated Dec. 1, 2014", 8 pgs.
"U.S. Appl. No. 12/288,034, Non Final Office Action dated May 8, 2014", 8 pgs.
"U.S. Appl. No. 12/288,034, Non Final Office Action dated Jun. 22, 2012", 7 pgs.
"U.S. Appl. No. 12/288,034, Response filed Feb. 4, 2014 to Final Office Action dated Nov. 4, 2013", 12 pgs.
"U.S. Appl. No. 12/288,034, Response filed May 1, 2012 to Restriction Requirement dated Nov. 3, 2011", 4 pgs.
"U.S. Appl. No. 12/288,034, Response filed Aug. 1, 2014 to Non Final Office Action dated May 8, 2014", 11 pgs.
"U.S. Appl. No. 12/288,034, Response filed Dec. 21, 2012 to Non Final Office Action dated Jun. 22, 2012", 12 pgs.
"U.S. Appl. No. 12/288,034, Restriction Requirement dated Nov. 3, 2011", 9 pgs.
"U.S. Appl. No. 12/288,045, Restriction Requirement dated Nov. 16, 2011", 9 pgs.
"U.S. Appl. No. 12/315,015, Advisory Action dated Apr. 7, 2014", 3 pgs.
"U.S. Appl. No. 12/315,015, Advisory Action dated Sep. 12, 2012", 3 pgs.
"U.S. Appl. No. 12/315,015, Examiner Interview Summary dated Nov. 28, 2014", 3 pgs.
"U.S. Appl. No. 12/315,015, Final Office Action dated Jan. 28, 2014", 8 pgs.
"U.S. Appl. No. 12/315,015, Final Office Action dated Apr. 26, 2012", 7 pgs.
"U.S. Appl. No. 12/315,015, Final Office Action dated Dec. 5, 2014", 9 pgs.
"U.S. Appl. No. 12/315,015, Non Final Office Action dated Mar. 30, 2015", 10 pgs.
"U.S. Appl. No. 12/315,015, Non Final Office Action dated Aug. 4, 2014", 7 pgs.
"U.S. Appl. No. 12/315,015, Non Final Office Action dated Sep. 27, 2013", 7 pgs.
"U.S. Appl. No. 12/315,015, Preliminary Amendment filed Mar. 10, 2009", 3 pgs.
"U.S. Appl. No. 12/315,015, Response filed Mar. 5, 2015 to Final Office Action dated Dec. 5, 2014", 13 pgs.
"U.S. Appl. No. 12/315,015, Response filed Mar. 28, 2014 to Final Office Action dated Jan. 24, 2014", 5 pgs.
"U.S. Appl. No. 12/315,015, Response filed Apr. 6, 2012 to Non Final Office Action dated Oct. 6, 2011", 12 pgs.
"U.S. Appl. No. 12/315,015, Response filed Jun. 17, 2014 to Final Office Action dated Jan. 28, 2014", 7 pgs.
"U.S. Appl. No. 12/315,015, Response filed Aug. 27, 2012 to Final Office Action dated Apr. 26, 2012", 6 pgs.
"U.S. Appl. No. 12/315,015, Response filed Nov. 4, 2014 to Non-Final Office Action dated Aug. 4, 2014", 7 pgs.
"U.S. Appl. No. 12/315,015, Response filed Dec. 27, 2013 to Non Final Office Action dated Sep. 27, 2013", 7 pgs.
Non Final Office Action dated Oct. 31, 2011, for U.S. Appl. No. 11/488,305, filed Jul. 18, 2006, 6 pages.
Non Final Office action dated May 18, 2004, for U.S. Appl. No. 10/271,334, filed Oct. 15, 2002, 8 pages.
Examiner's Interview Summary dated Feb. 11, 2005, for U.S. Appl. No. 10/271,334, filed Oct. 15, 2002, 1 page.
Notice of Allowability dated Feb. 11, 2005, for U.S. Appl. No. 10/271,334, filed Oct. 15, 2002, 4 pages.
Notice of Allowance dated Mar. 17, 2005, for U.S. Appl. No. 10/271,334, filed Oct. 15, 2002, 3 pages.
Notice of Allowance dated Aug. 26, 2005, for U.S. Appl. No. 10/271,334, filed Oct. 15, 2002, 3 pages.
Non-Final Office Action dated May 5, 2009, for U.S. Appl. No. 11/166,411, filed Jun. 24, 2005, 7 pages.
Final Office Action dated Dec. 3, 2009, for U.S. Appl. No. 11/166,411, filed Jun. 24, 2005, 5 pages.
Notice of Allowance dated Jan. 6, 2011, for U.S. Appl. No. 11/166,411, filed Jun. 24, 2005, 4 pages.
Non-Final Office Action dated Oct. 6, 2008, for U.S. Appl. No. 11/540,427, filed Sep. 29, 2006, 9 pages.
Final Office Action dated Jul. 21, 2009, for U.S. Appl. No. 11/540,427, filed Sep. 29, 2006, 8 pages.
Notice of Allowance dated Apr. 29, 2011, for U.S. Appl. No. 11/540,427, filed Sep. 29, 2006, 8 pages.
Non-Final Office Action dated Nov. 12, 2010, for U.S. Appl. No. 11/540,428, filed Sep. 29, 2006, 7 pages.
Non-Final Office Action dated May 20, 2010, for U.S. Appl. No. 11/978,752, filed Oct. 30, 2007, 5 pages.
Final Office Action dated Dec. 22, 2010, for U.S. Appl. No. 11/978,752, filed Oct. 30, 2007, 6 pages.
Non-Final Office Action dated Sep. 3, 2010, for U.S. Appl. No. 11/978,753, filed Oct. 30, 2007, 7 pages.
Final Office Action dated May 2, 2011, for U.S. Appl. No. 11/978,753, filed Oct. 30, 2007, 8 pages.
Non-Final Office Action dated Jan. 27, 2006, for U.S. Appl. No. 10/669,881, filed Sep. 24, 2003, 5 pages.
Final Office Action dated Jan. 25, 2008, for U.S. Appl. No. 10/669,881, filed Sep. 24, 2003, 7 pages.
Notice of Allowance dated Oct. 8, 2008, for U.S. Appl. No. 10/669,881, filed Sep. 24, 2003, 6 pages.
Non-Final Office Action dated May 14, 2008, for U.S. Appl. No. 11/255,116, filed Oct. 20, 2005, 14 pages.
Notice of Allowance dated Aug. 10, 2009, for U.S. Appl. No. 11/255,116, filed Oct. 20, 2005, 4 pages.
Non-Final Office Action dated Sep. 1, 2010, for U.S. Appl. No. 11/488,305, filed Jul. 18, 2006, 7 pages.
Final Office Action dated Apr. 13, 2011, for U.S. Appl. No. 11/488,305, filed Jul. 18, 2006, 8 pages.
International Search Report dated Mar. 6, 2003, for PCT Patent Application No. PCT/US02/32753, filed on Oct. 15, 2002, one page.

(56) References Cited

OTHER PUBLICATIONS

Written Opinion dated Aug. 26, 2003, for PCT Patent Application No. PCT/US02/32753, filed on Oct. 15, 2002, 4 pages.
International Preliminary Report on Patentability dated Sep. 1, 2004, for PCT Patent Application No. PCT/US02/32753, filed on Oct. 15, 2002, 3 pages.
International Search Report dated May 8, 2003, for PCT Patent Application No. PCT/US02/38365, filed on Nov. 29, 2002, 4 pages.
Written Opinion dated Oct. 27, 2003, for PCT Patent Application No. PCT/US02/38365, filed on Nov. 29, 2002, 4 pages.
International Preliminary Report on Patentability dated Mar. 1, 2004, for PCT Patent Application No. PCT/US02/38365, filed on Nov. 29, 2002, 3 pages.
International Search Report dated Feb. 24, 2006, for PCT Patent Application No. PCT/US2004/029402, filed on Sep. 10, 2004, 3 pages.
Written Opinion dated Feb. 24, 2006, for PCT Patent Application No. PCT/US2004/029402, filed on Sep. 10, 2004, 3 pages.
International Preliminary Report on Patentability dated Jul. 10, 2006, for PCT Patent Application No. PCT/US2004/029402, filed on Sep. 10, 2004, 3 pages.
International Search Report dated Mar. 30, 2007, for PCT Patent Application No. PCT/US2006/033741, filed on Aug. 29, 2006, 2 pages.
Written Opinion dated Mar. 30, 2007, for PCT Patent Application No. PCT/US2006/033741, filed on Aug. 29, 2006, 4 pages.
International Preliminary Report on Patentability dated Jul. 28, 2007, for PCT Patent Application No. PCT/US2006/033741, filed on Aug. 29, 2006, 5 pages.
International Search Report dated Aug. 15, 2007, for PCT Patent Application No. PCT/US2006/033748, filed on Aug. 29, 2006, 3 pages.
Written Opinion dated Aug. 15, 2007, for PCT Patent Application No. PCT/US2006/033748, filed on Aug. 29, 2006, 5 pages.
International Preliminary Report on Patentability dated Jun. 18, 2008, for PCT Patent Application No. PCT/US2006/033748, filed on Aug. 29, 2006, 7 pages.
International Search Report dated Aug. 15, 2007, for PCT Patent Application No. PCT/US06/033749, filed on Aug. 29, 2006, 3 pages.
Written Opinion dated Aug. 15, 2007, for PCT Patent Application No. PCT/US06/033749, filed on Aug. 29, 2006, 5 pages.
International Preliminary Report on Patentability dated Jun. 18, 2008, for PCT Patent Application No. PCT/US06/033749, filed on Aug. 29, 2006, 6 pages.
International Search Report dated Jul. 8, 2008, for PCT Patent Application No. PCT/US2006/033747, filed on Aug. 29, 2006, published on Apr. 26, 2007, 2 pages.
Written Opinion dated Jul. 8, 2008, for PCT Patent Application No. PCT/US2006/033747, filed on Aug. 29, 2006, 3 pages.
International Search Report dated Aug. 30, 2007, for PCT Patent Application No. PCT/US2006/037085, filed on Sep. 22, 2006, one page.
Written Opinion dated Aug. 30, 2007, for PCT/US2006/037085, filed on Sep. 22, 2006, 7 pages.
International Preliminary Report on Patentability dated Jul. 24, 2008, for PCT/US2006/037085, filed on Sep. 22, 2006, 9 pages.
International Search Report dated Dec. 11, 2009, for PCT/US2009/005604, filed on Oct. 14, 2009, 3 pages.
Written Opinion dated Dec. 11, 2009, for PCT/US2009/005604, filed on Oct. 14, 2009, 7 pages.
International Search Report dated Dec. 18, 2009, for PCT/US2009/005609, filed Oct. 14, 2009, 3 pages.
"U.S. Appl. No. 10/271,334, Non Final Office Action dated May 18, 2004", 9 pgs.
"U.S. Appl. No. 10/271,334, Notice of Allowance dated Feb. 11, 2005", 6 pgs.
"U.S. Appl. No. 10/271,334, Notice of Allowance dated Aug. 26, 2005", 3 pgs.
"U.S. Appl. No. 10/271,334, Response filed Mar. 15, 2004 to Restriction Requirement dated Sep. 23, 2003", 1 pg.
"U.S. Appl. No. 10/271,334, Response filed Nov. 22, 2004 to Non Final Office Action dated May 18, 2004", 6 pgs.
"U.S. Appl. No. 10/271,334, Restriction Requirement dated Sep. 23, 2003", 4 pgs.
"U.S. Appl. No. 10/271,334, Supplemental Response filed Jan. 28, 2005 to Non Final Office Action dated May 18, 2004", 6 pgs.
"U.S. Appl. No. 10/307,226, 312 Amendment filed Oct. 24, 2011", 3 pgs.
"U.S. Appl. No. 10/307,226, Appeal Brief filed Oct. 14, 2010", 15 pgs.
"U.S. Appl. No. 10/307,226, Final Office Action dated Jun. 27, 2008", 6 pgs.
"U.S. Appl. No. 10/307,226, Final Office Action dated Dec. 12, 2006", 5 pgs.
"U.S. Appl. No. 10/307,226, Non Final Office Action dated Mar. 13, 2006", 6 pgs.
"U.S. Appl. No. 10/307,226, Non Final Office Action dated Jun. 12, 2007", 5 pgs.
"U.S. Appl. No. 10/307,226, Non Final Office Action dated Sep. 9, 2009", 16 pgs.
"U.S. Appl. No. 10/307,226, Notice of Allowance dated Jul. 22, 2011", 8 pgs.
"U.S. Appl. No. 10/307,226, Preliminary Amendment filed Jul. 22, 2005", 3 pgs.
"U.S. Appl. No. 10/307,226, PTO Response to 312 Amendment dated Nov. 10, 2011", 3 pgs.
"U.S. Appl. No. 10/307,226, Response filed Apr. 9, 2007 to Final Office Action dated Dec. 12, 2006", 7 pgs.
"U.S. Appl. No. 10/307,226, Response filed Jun. 23, 2009 to Final Office Action dated Jun. 27, 2008", 10 pgs.
"U.S. Appl. No. 10/307,226, Response filed Sep. 15, 2006 to Non Final Office Action dated Mar. 13, 2006", 6 pgs.
"U.S. Appl. No. 10/307,226, Response filed Dec. 14, 2007 to Non Final Office Action dated Jun. 12, 2007", 7 pgs.
"U.S. Appl. No. 10/669,881, Final Office Action dated Jan. 25, 2008", 7 pgs.
"U.S. Appl. No. 10/669,881, Non Final Office Action dated Jan. 27, 2006", 5 pgs.
"U.S. Appl. No. 10/669,881, Notice of Allowance dated Oct. 8, 2008", 16 pgs.
"U.S. Appl. No. 10/669,881, Preliminary Amendment dated May 6, 2005", 3 pgs.
"U.S. Appl. No. 10/669,881, Response filed Mar. 11, 2008 to Final Office Action dated Jan. 25, 2008", 8 pgs.
"U.S. Appl. No. 10/669,881, Response filed May 15, 2006 Non Final Office Action dated Jan. 27, 2006", 9 pgs.
"U.S. Appl. No. 10/669,881, Response filed Sep. 7, 2007 Restriction Requirement dated Jun. 19, 2007", 4 pgs.
"U.S. Appl. No. 10/669,881, Response filed Oct. 2, 2006 Restriction Requirement dated Jul. 27, 2006", 6 pgs.
"U.S. Appl. No. 10/669,881, Restriction Requirement dated Jul. 27, 2006", 5 pgs.
"U.S. Appl. No. 10/669,881, Restriction Requirement dated Jun. 19, 2007", 5 pgs.
"U.S. Appl. No. 10/692,282, Non Final Office Action dated Aug. 30, 2005", 6 pgs.
"U.S. Appl. No. 10/692,282, Notice of Allowance dated Jun. 13, 2006", 6 pgs.
"U.S. Appl. No. 10/692,282, Response filed Feb. 22, 2005 to Restriction Requirement dated Aug. 17, 2004", 4 pgs.
"U.S. Appl. No. 10/692,282, Response filed Feb. 28, 2006 to Non Final Office Action dated Aug. 30, 2005", 5 pgs.
"U.S. Appl. No. 10/692,282, Restriction Requirement dated Aug. 17, 2004", 6 pgs.
"U.S. Appl. No. 10/693,255, Examiner Interview Summary dated Feb. 17, 2005", 3 pgs.
"U.S. Appl. No. 10/693,255, Non Final Office action dated Dec. 9, 2004", 6 pgs.
"U.S. Appl. No. 10/693,255, Notice of Allowance dated Mar. 9, 2005", 9 pgs.

(56) References Cited

OTHER PUBLICATIONS

"U.S. Appl. No. 10/693,255, Response filed Feb. 17, 2005 to Non Final Office action dated Dec. 9, 2004", 6 pgs.
"U.S. Appl. No. 10/752,435, Final Office Action dated May 14, 2010", 8 pgs.
"U.S. Appl. No. 10/752,435, Final Office Action dated Jul. 12, 2007", 8 pgs.
"U.S. Appl. No. 10/752,435, Final Office Action dated Dec. 8, 2008", 8 pgs.
"U.S. Appl. No. 10/752,435, Non Final Office Action dated Mar. 18, 2008", 7 pgs.
"U.S. Appl. No. 10/752,435, Non Final Office Action dated Jul. 21, 2009", 7 pgs.
"U.S. Appl. No. 10/752,435, Non Final Office Action dated Oct. 19, 2006", 17 pgs.
"U.S. Appl. No. 10/752,435, Response filed Jan. 9, 2008 to Final Office Action dated Jul. 12, 2007", 10 pgs.
"U.S. Appl. No. 10/752,435, Response filed Jan. 25, 2010 to Non Final Office Action dated Jul. 21, 2009", 9 pgs.
"U.S. Appl. No. 10/752,435, Response filed Apr. 9, 2007 to Non Final Office Action dated Oct. 19, 2006", 13 pgs.
"U.S. Appl. No. 10/752,435, Response filed May 12, 2009 to Final Office Action dated Dec. 8, 2008", 9 pgs.
"International Application Serial No. PCT/US2009/005609, International Preliminary Report on Patentability dated Jan. 9, 2011", 9 pgs.
"Japanese Application Serial No. 2003-546789, Office Action dated Feb. 26, 2009", w/English translation, 7 pgs.
"Japanese Application Serial No. 2003-546789, Office Action dated Jun. 17, 2008", w/English translation, 6 pgs.
"Japanese Application Serial No. 2003-546789, Office Action dated Oct. 7, 2009", 3 pgs.
"Japanese Application Serial No. 2003-546789, Response filed May 21, 2009 to Office Action dated Feb. 26, 2009", 6 pgs.
"Japanese Application Serial No. 2003-546789, Response filed Dec. 11, 2008 to Office Action dated Jun. 17, 2008", w/English translation, 9 pgs.
"Japanese Application Serial No. 2006-528036, Office Action dated Jan. 19, 2010", 3 pgs.
"Japanese Application Serial No. 2006-528036, Office Action dated Feb. 26, 2009", w/English translation 5 pgs.
"Japanese Application Serial No. 2006-528036, Office Action dated Jun. 23, 2008", w/English translation 5 pgs.
"Japanese Application Serial No. 2006-528036, Response filed Dec. 25, 2008 to Office Action dated Jun. 23, 2008", w/English translation 9 pgs.
"Japanese Application Serial No. 2006-536616, Office Action dated Jun. 23, 2008", 8 pgs.
"Japanese Application Serial No. 2006-536616, Response filed Dec. 19, 2008 to Office Action dated Jun. 23, 2008", 9 pgs.
"Japanese Application Serial No. 2006-536617, Office Action dated Jun. 17, 2008", English only, 3 pgs.
"Japanese Application Serial No. 2006-536617, Response filed May 12, 2009 to Office Action dated Jun. 17, 2008", 19 pgs.
"Japanese Application Serial No. 2006-547608, Office Action dated Jun. 23, 2008", 5 pgs.
"Japanese Application Serial No. 2006-547608, Response filed Dec. 19, 2008 to Office Action dated Jun. 23, 2008", 10 pgs.
"Japanese Application Serial No. 2007500928, Office Action dated Jul. 1, 2010", wlEnglish translation, 10 pgs.
"Japanese Application Serial No. 2007504965, Office Action dated Mar. 7, 2012", wlEnglish translation, 4 pgs.
"Japanese Application Serial No. 2007504965, Office Action dated Jun. 14, 2011", wlEnglish translation, 4 pgs.
"Japanese Application Serial No. 2007504965, Office Action dated Sep. 14, 2010", English translation, 1 pg.
"Japanese Application Serial No. 2007504965, Response filed Mar. 11, 2011 to Office Action dated Sep. 14, 2010", 8 pgs.
"Japanese Application Serial No. 2008-306790, Office Action dated May 31, 2011", 1 pg.
"Japanese Application Serial No. 2008-306790, Response filed Nov. 29, 2011 to Office Action dated May 8, 2012", 2 pgs.
"Japanese Application Serial No. 2008-306790, Response filed Nov. 29, 2011 to Office Action dated May 31, 2011", 12 pgs.
"Japanese Application Serial No. 2008-316282, Office Action dated May 16, 2011", 2 pgs.
"Japanese Application Serial No. 2008-316296, Office Action dated Feb. 28, 2011", 2 pgs.
"Japanese Application Serial No. 2008-316296, Office Action dated Jun. 22, 2010", 2 pgs.
Japanese Application Serial No. 2008-323279, Office Action dated Sep. 30, 2010, 1 pg.
"Japanese Application Serial No. 2008-323290, Office Action dated Jun. 6, 2012", 8 pgs.
"Japanese Application Serial No. 2008-323290, Office Action dated Jun. 8, 2011", 8 pgs.
"Japanese Application Serial No. 2008-323290, Response filed Dec. 7, 2011 to Office Action dated Jun. 8, 2011", 16 pgs.
"Japanese Application Serial No. 2008-536574, Office Action dated Mar. 11, 2010", English only, 4 pgs.
"Japanese Application Serial No. 2008-536574, Office Action dated Oct. 3, 2011", 7 pgs.
"Japanese Application Serial No. 2008-536575, Office Action dated Jul. 7, 2011", 5 pgs.
"Japanese Application Serial No. 2008-536576, Office Action dated Jul. 19, 2011", 4 pgs.
"Japanese Application Serial No. 2008-536577, Notice of Allowance dated May 30. 2012", 3 pgs.
"Japanese Application Serial No. 2008-536577, Office Action dated Jul. 8, 2011", w/English translation, 4 pgs.
"Japanese Application Serial No. 2008-536577, Response filed Jan. 6, 2012 to Office Action dated Jul. 8, 2011", 3 pgs.
"5mm Origin Tracker It Runs in Circles Around Staples", Guidant Origin Advertising Literature, (1995), 2 pgs.
Anonymous. (1995). "5mm Origin Tacker™ It Runs in Circles Around Staples," Guidant Origin Advertising Literature, 2 pages.
Bolduc, Lee, "Devices, Systems, and Method for Prosthesis Delivery and Implantation, Including the Use of a Fastener Tool", U.S. Appl. No. 12/917,842, filed Nov. 2, 2010, 120 pgs.
Gadacz, T. et al. (Nov. 1995). "The Spiral Tacker: A New Technique for Stabilizing Prosthetic Mesh in Laparoscopic Hernia Repair," Surgical Rounds 461-467.
Hatchett, R.L. et al. (1995). "Extraperitoneal Endoscopic Burch Repair Using a Tacker Mesh Technique," Circa 1-4.
Medical Technologies. (Oct. 1995). "Laparoscopic Surgery," Medical Data International, Inc. MedPro p. 190.
Newman, L. et al., "Tacker-Assisted TAPP Procedure", (1995), Circa 2 pgs.
Non Final Office Action dated May, 10, 2012, for U.S. Appl. No. 12/288,031, filed Oct. 16, 2008 for Bolduc et al., 8 pages.
Notice of Allowance dated Aug. 23, 2011, for U.S. Appl. No. 11/166,411, filed Jun. 24, 2005, 5 pages.
Final Office Action dated Aug. 4, 2011, for U.S. Appl. No. 11/540,428, filed Sep. 29, 2006, 9 pages.
Notice of Allowance dated Aug. 31, 2011, for U.S. Appl. No. 11/978,752, filed Oct. 30 2007, 5 pages.
Non-Final Office Action dated Oct. 6, 2011, for U.S. Appl. No. 12/315,015, filed Nov. 26, 2008, 10 pages.
"European Application Serial No. 06802580.8, Office Action dated Feb. 25, 2013", 3 pgs.
"European Application Serial No. 06802580.8, Response filed Apr. 17, 2014 to Extended European Search Report dated Sep. 24, 2013", 2 pgs.
"European Application Serial No. 09075319.5, Extended European Search Report dated Oct. 14, 2009", 6 pgs.
"European Application Serial No. 09075319.5, Office Action dated Jan. 14, 2010", 1 pgs.
"European Application Serial No. 09075319.5, Office Action dated Oct. 14, 2010", 4 pgs.
"European Application Serial No. 09075319.5, Response filed Feb. 21, 2011 to Office Action dated Oct. 14, 2010", 5 pgs.
"European Application Serial No. 09075319.5, Response filed Jul. 20, 2010 to Office Action dated Jan. 14, 2010", 13 pgs.

(56) References Cited

OTHER PUBLICATIONS

"European Application Serial No. 09820886.1, Extended European Search Report dated Mar. 27, 2015", 8 pgs.
"European Application Serial No. 09820886.1, Office Action dated Jun. 7, 2011", 2 pgs.
"European Application Serial No. 09820886.1, Response filed Dec. 8, 2011 to Office Action dated Jun. 7, 2011", 3 pgs.
"European Application Serial No. 09820891.1, Office Action dated Jun. 7, 2011", 2 pgs.
"European Application Serial No. 09820891.1, Response filed Dec. 8, 2011 to Office Action dated Jun. 7, 2011", 2 pgs.
"German Application Serial No. 10297483.7, Office Action dated Jan. 9, 2006", 4 pgs.
"German Application Serial No. 10297483.7, Office Action dated Jul. 8, 2006", 2 pgs.
"German Application Serial No. 10297483.7, Office Action mailed and Response filed Oct. 30, 2006", 8 pgs.
"German Application Serial No. 10297483.7, Response filed Jul. 7, 2006 to Office Action dated Jan. 9, 2006", 14 pgs.
"German Application Serial No. 10297483.7, Response filed Oct. 26, 2006 to Office Action dated Jul. 8, 2006", 3 pgs.
"Great Britain Application Serial No. 0411107.6, Office Action dated Feb. 28, 2005", 3 pgs.
"Great Britain Application Serial No. 0411107.6, Office Action dated Sep. 29, 2005", 1 pg.
"Great Britain Application Serial No. 0411107.6, Response filed Aug. 23, 2005 to Office Action dated Feb. 28, 2005", 3 pgs.
"Great Britain Application Serial No. 0411107.6, Response filed Oct. 31, 2005 to Office Action dated Sep. 29, 2005", 4 pgs.
"Great Britain Application Serial No. 0522152.8, Office Action dated Dec. 5, 2005", 5 pgs.
"Great Britain Application Serial No. 0522152.8, Response filed Apr. 26, 2006 to Office Action dated Dec. 5, 2005", 48 pgs.
"International Application Serial No. PCT/US2002/032753, International Preliminary Examination Report dated Aug. 16, 2004", 3 pgs.
"International Application Serial No. PCT/US2002/032753, International Search Report dated Mar. 6, 2003", 1 pg.
"International Application Serial No. PCT/US2004/027589, International Preliminary Report on Patentability dated Apr. 6, 2005", 4 pgs.
"International Application Serial No. PCT/US2004/027589, International Search Report dated Apr. 6, 2005", 1 pg.
"International Application Serial No. PCT/US2004/027589, Written Opinion dated Apr. 6, 2005", 3 pgs.
"International Application Serial No. PCT/US2004/027590, International Preliminary Examination Report dated Feb. 16, 2006", 3 pgs.
"International Application Serial No. PCT/US2004/027590, International Search Report dated Jan. 12, 2005", 1 pg.
"International Application Serial No. PCT/US2004/027590, Written Opinion dated Jan. 12, 2005", 3 pgs.
"International Application Serial No. PCT/US2005/00059, International Preliminary Report on Patentability dated May 18, 2007", 8 pgs.
"International Application Serial No. PCT/US2005/00059, International Search Report dated Jan. 5, 2007", 3 pgs.
"International Application Serial No. PCT/US2005/00059, Written Opinion dated Jan. 5, 2007", 8 pgs.
"International Application Serial No. PCT/US2005/005453, International Preliminary Examination Report dated Mar. 13, 2006", 3 pgs.
"International Application Serial No. PCT/US2005/005453, International Preliminary Report on Patentability dated Feb. 16, 2006", 3 pgs.
"International Application Serial No. PCT/US2005/005453, International Search Report dated Aug. 30, 2005", 1 pg.
"International Application Serial No. PCT/US2005/005453, International Written Opinion dated Aug. 30, 2005", 3pgs.
"International Application Serial No. PCT/US2005/005627, International Preliminary Examination Report dated Apr. 7, 2009", 3 pgs.
"International Application Serial No. PCT/US2005/005627, International Search Report dated Sep. 25, 2007", 1 pg.
"International Application Serial No. PCT/US2005/005627, Written Opinion dated Sep. 25, 2007", 3 pgs.
"International Application Serial No. PCT/US2006/033747, International Preliminary Report on Patentability dated Mar. 1, 2011", 4 pgs.
"International Application Serial No. PCT/US2009/005604, International Preliminary Report on Patentability dated Jan. 13, 2011", 10 pgs.
"International Application Serial No. PCT/US2009/005607, International Preliminary Report on Patentability dated Jan. 9, 2011", 9 pgs.
"International Application Serial No. PCT/US2009/005607, International Search Report dated Dec. 11, 2009", 2 pgs.
"International Application Serial No. PCT/US2009/005607, Written Opinion dated Dec. 11, 2009", 6 pgs.
"International Application Serial No. PCT/US2009/005608, International Preliminary Report on Patentability dated Jan. 14, 2011", 7 pgs.
"International Application Serial No. PCT/US2009/005608, International Search Report dated Dec. 10, 2009", 2 pgs.
"International Application Serial No. PCT/US2009/005608, Written Opinion dated Dec. 10, 2009", 4 pgs.

\* cited by examiner

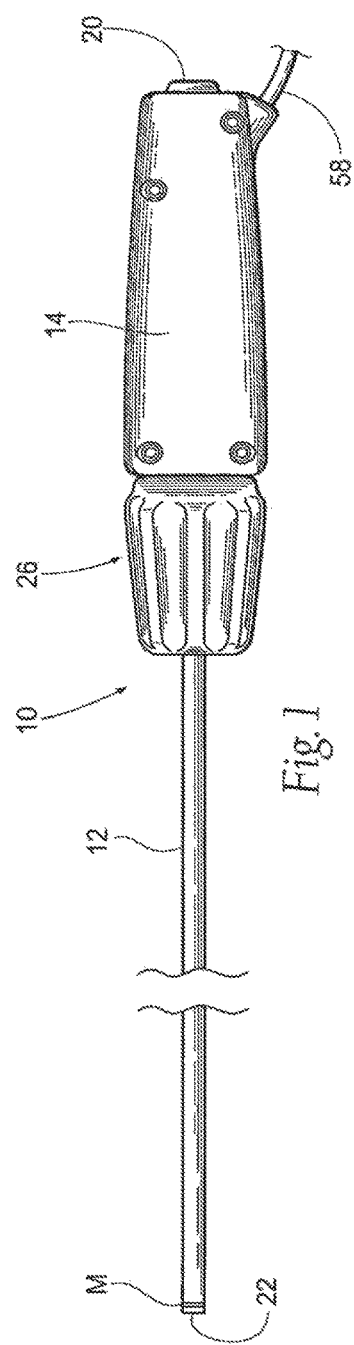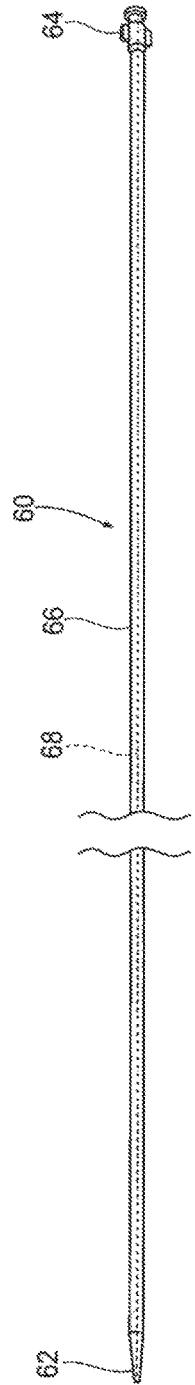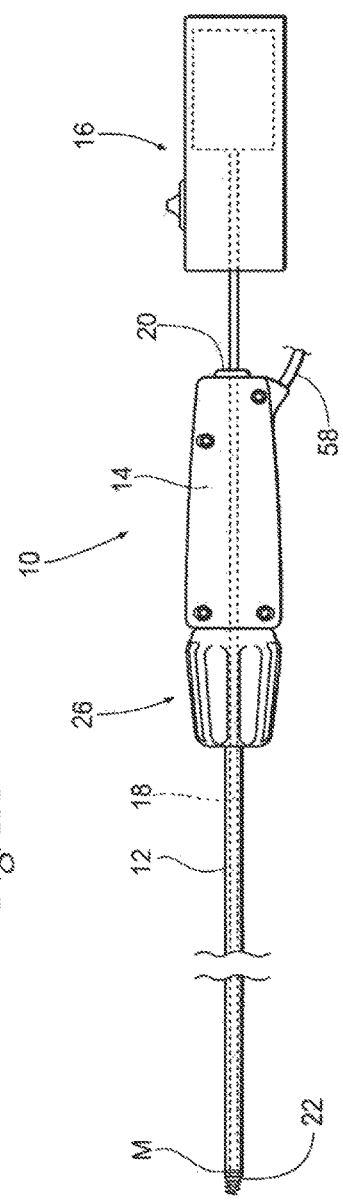

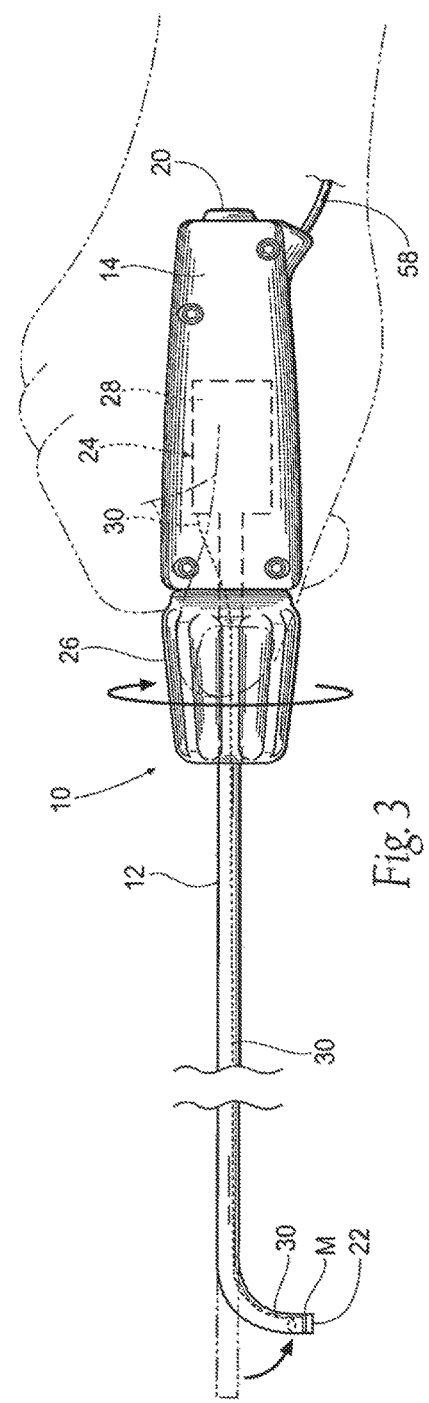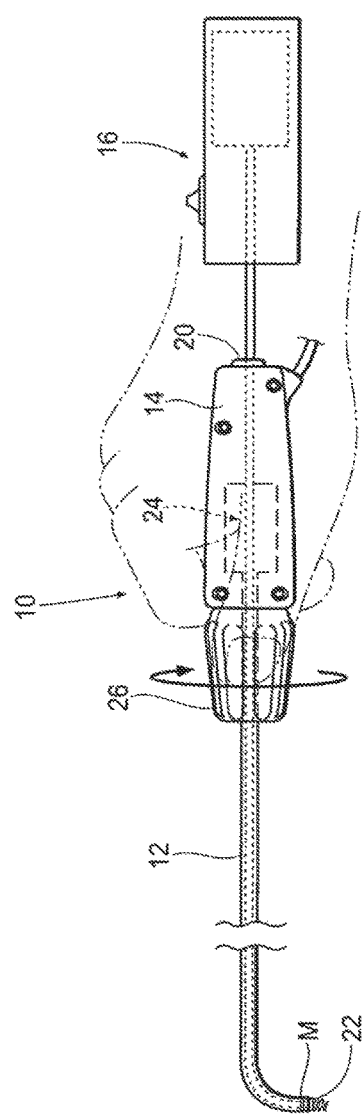
Fig. 3
Fig. 4

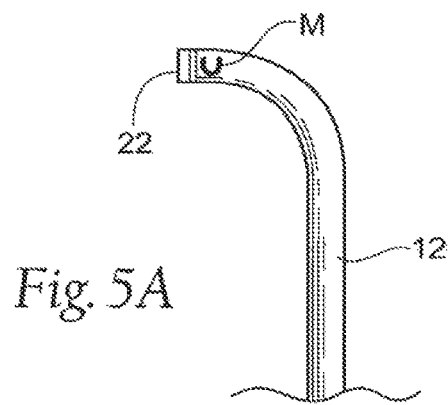
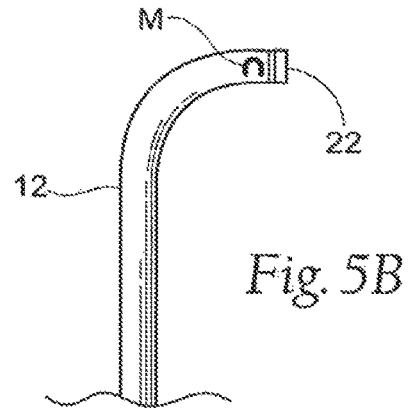
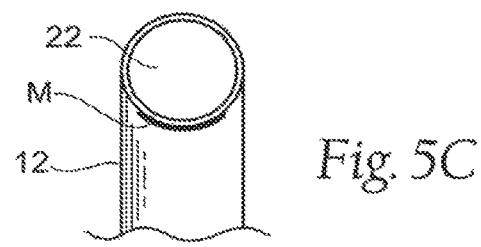
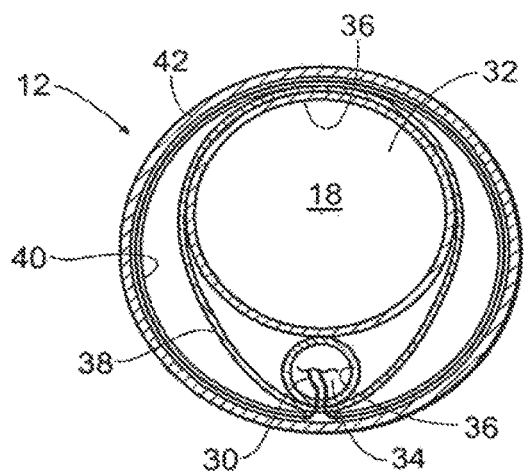

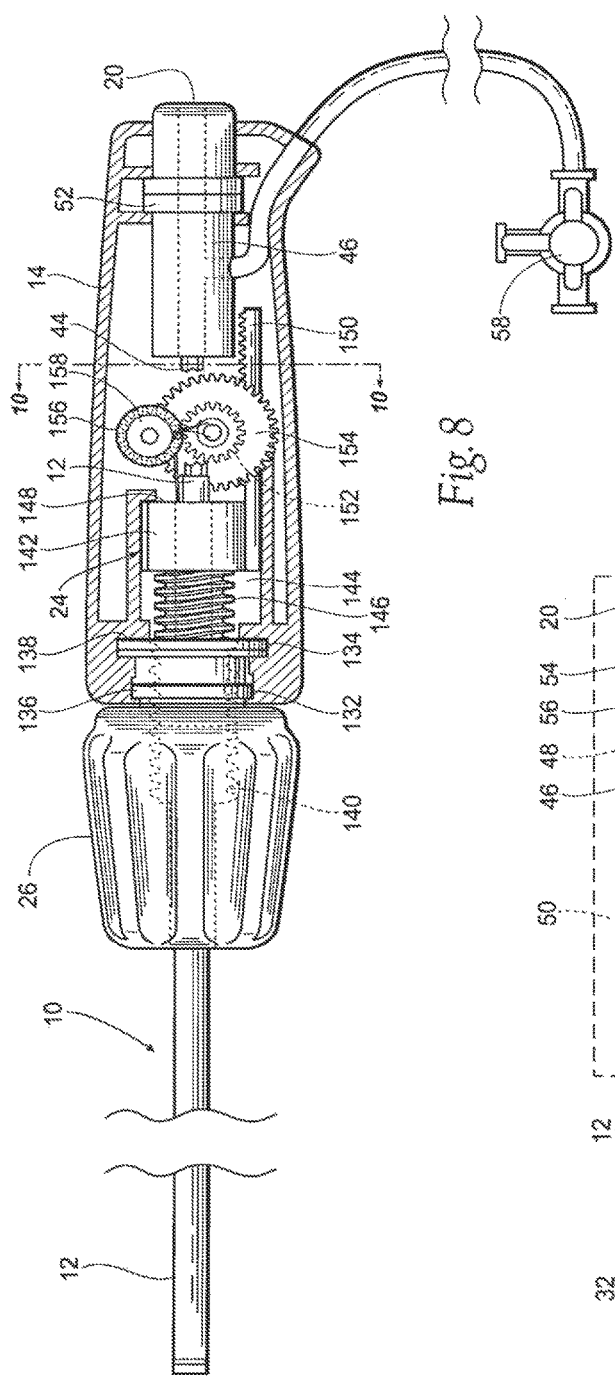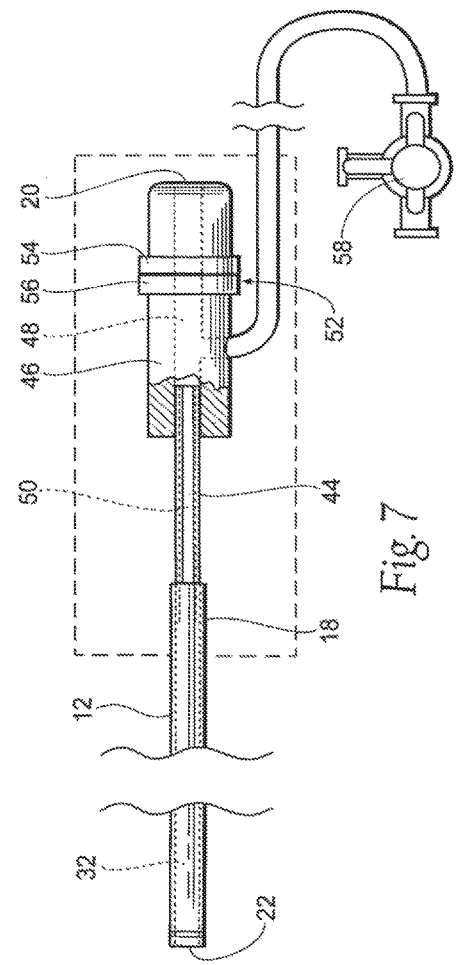

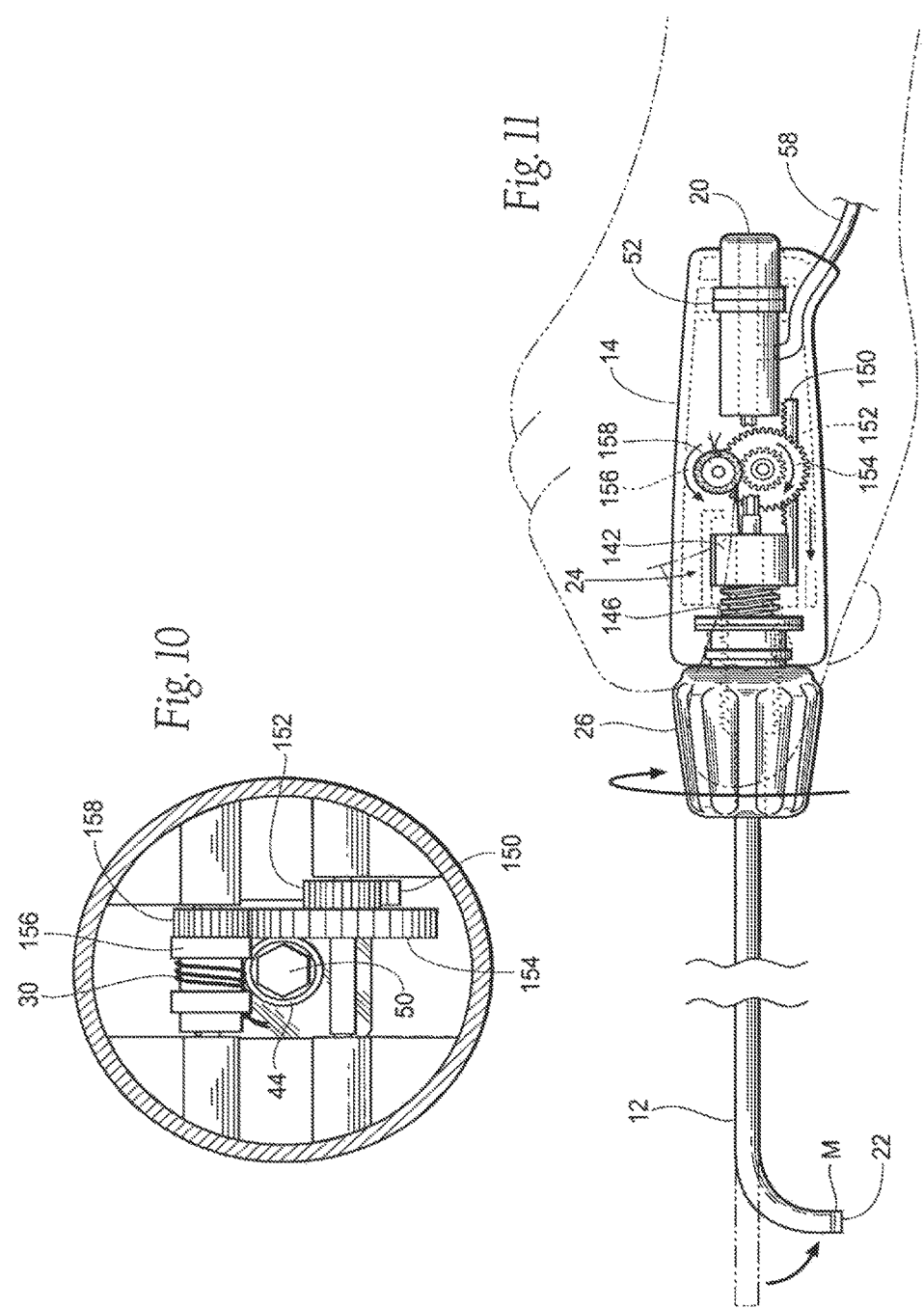

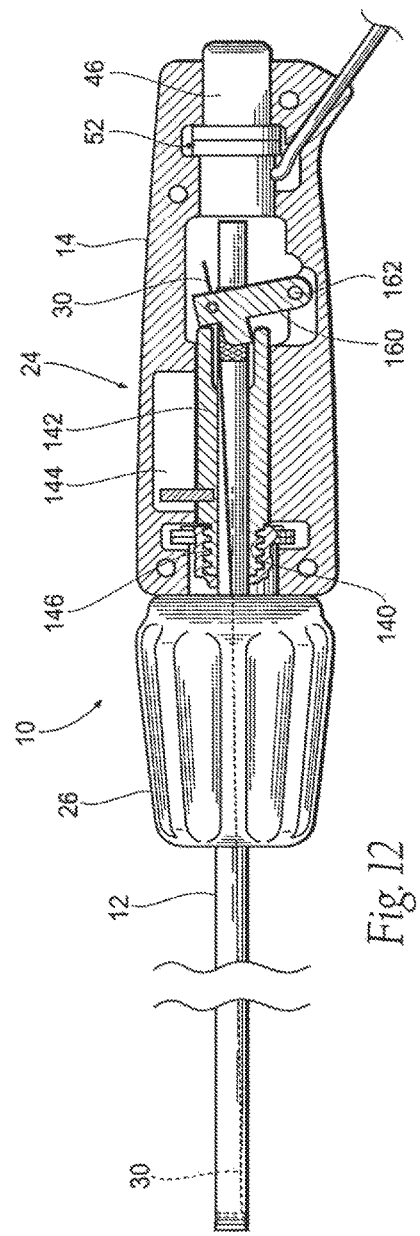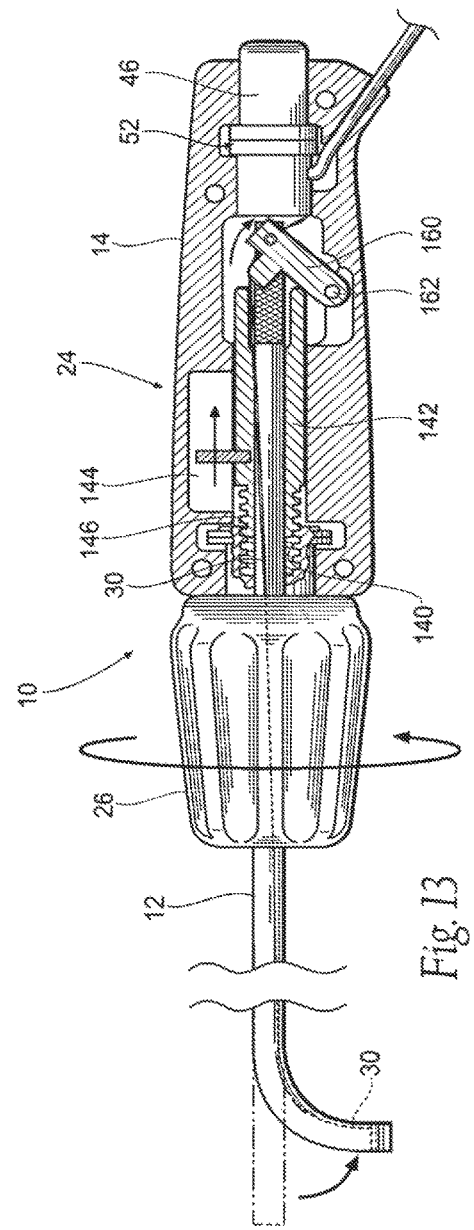

DEVICES, SYSTEM, AND METHODS FOR GUIDING AN OPERATIVE TOOL INTO AN INTERIOR BODY REGION

RELATED APPLICATIONS

This application is a continuation of co-pending U.S. patent application Ser. No. 11/254,619, filed Oct. 20, 2005, now allowed, which is a continuation-in-part of U.S. patent application Ser. No. 11/166,411, filed Jun. 24, 2005, (now U.S. Pat. No. 8,092,519), entitled "Endovascular Aneurysm Repair System," which is a divisional of U.S. patent application Ser. No. 10/271,334, filed Oct. 15, 2002 (now U.S. Pat. No. 6,960,217), which claims the benefit of U.S. Provisional Patent Application Ser. No. 60/333,937, filed Nov. 28, 2001, and entitled "Endovascular Aneurysm Repair System," which are each incorporated herein by reference. This application is also a continuation-in-part of U.S. patent application Ser. No. 10/307,226, filed Nov. 29, 2002, (now U.S. Pat. No. 8,075,570), and entitled "Intraluminal Prosthesis Attachment Systems and Methods" and a continuation-in-part of U.S. patent application Ser. No. 10/669,881, filed Sep. 24, 2003, (now U.S. Pat. No. 7,491,232), and entitled "Catheter-Based Fastener Implantation Apparatus and Methods with Implantation Apparatus and Methods with Implantation Force Resolution," which are each incorporated herein by reference.

FIELD OF THE INVENTION

This invention relates generally to devices, systems, and methods that guide operative tools within a vessel or hollow body organ.

BACKGROUND OF THE INVENTION

In the field of steerable guide systems, there is a need to translate a comfortable rotational manipulation by a physician into an effective distal deflection. There is also a need for a guide system that would provide a mechanical advantage such that a minimal manipulation by a physician would provide a sufficient distal deflection.

SUMMARY OF THE INVENTION

The invention provides improved devices, systems, and methods for guiding an operative tool for use within an interior tissue region.

According to one aspect of the invention, a guide device comprises a guide tube that establishes a guide passage through which an operative tool can be deployed into an interior body region for use. The device includes a steering assembly that, in use, deflects or bends the distal end region of the guide tube, so that the operative tool can be placed in a desired orientation with respect to tissue.

The steering assembly is desirable configured for single handed operation by the clinician. The steering assembly is also desirably configured to provide a mechanical advantage sufficient to translate relatively small increments of clinician control into relatively larger increments of guide tube deflection.

In one embodiment, the steering assembly includes a rack and pinion linkage system that translates rotation of an actuator into linear movement of a rack into rotation of a gear train, to apply a tension force to a deflecting component coupled to the distal end region of the guide tube.

In another embodiment, the steering assembly includes a pivoting lever system that translates rotation of an actuator into linear movement of a slider into pivotal movement of a lever arm, to apply a tension force to a deflecting component coupled to the distal end region of the guide tube.

In both embodiments, the tension applied to the deflecting component bends or deflects the distal end region of the guide tube.

In one embodiment, the operative tool applies one or more fasteners to tissue. The steerable guide device makes it possible to accurately orient and maintain the fastening tool with respect to tissue, without the need to place a steering mechanism on-board the fastening tool or without the need to equip the fastening tool with a guide wire lumen.

BRIEF DESCRIPTION OF THE DRAWINGS

FIG. 1 is a plane view of a steerable guide device in its straightened, undeflected position.

FIG. 1A is a plan view of a dilator for use with the steerable guide device of FIG. 1.

FIG. 2 is a plane view of the steerable guide device shown in FIG. 1 in association with an operative tool.

FIG. 3 is a plane view of the steerable guide system shown in FIG. 1, showing a clinician's hand rotating an actuator knob to operate an associated steering assembly to cause bending or deflection of the distal end region of the device.

FIG. 4 is a plane view of the steerable guide device shown in FIG. 3 in association with on operative tool.

FIGS. 5A, 5B, and 5C are plane views of the distal end region of the device shown in FIG. 4, showing the presence of a radiopaque marker that is shaped to provide a different visual image depending upon its orientation, respectively, anteriorly (FIG. 5A), posteriorly (FIG. 5B), or laterally (FIG. 5C).

FIG. 6A is an interior section view of the distal end region, of the device shown in FIG. 3, taken generally along line 6A-6A of FIG. 6B.

FIG. 7 is a plane view, partially diagrammatic, showing the attachment of the guide tube of the device to the handle of the device, and the formation of an interior passage through the handle and guide tube to receive an operative tool.

FIG. 8 is a plane side view, of the device shown in FIG. 1, with the handle broken away and in section to show the components of the steering assembly within the handle, the operation of which bends or deflects the distal end region in the manner shown in FIG. 3.

FIG. 10 is a section view taken generally along line 10-10 in FIG. 8.

FIG. 11 is a plane side view, of the device shown in FIG. 3, with the handle broken away and in section to show the operation of the steering assembly within the handle to bends or deflects the distal end region of the device.

FIG. 12 is side plane view of a steerable guide device, with the handle broken away and in section, showing an alternative steering assembly in its neutral position, in which the distal end region of the guide tube is straight and undeflected.

FIG. 13 is side plane view of a steerable guide device shown in FIG. 12, with the handle broken away and in section, showing the operation of the alternative steering assembly to bend or deflect the distal end region of the guide tube.

DESCRIPTION OF PREFERRED EMBODIMENTS

Figure 6B:
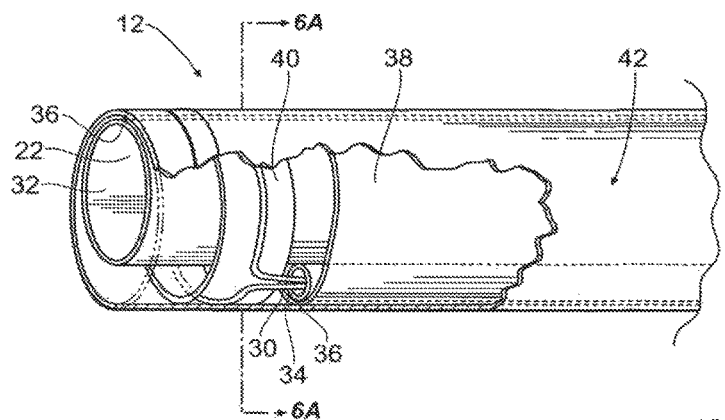
FIG. 6B is a perspective end view, partially broken away, of the distal end region of the device shown in section in FIG. 6A.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Overview

FIG. 1 shows a steerable guide device 10. The steerable guide device 10 comprises a flexible guide tube 12 carried by a handle 14. The illegible guide tube 12 may be constructed, for example, by extrusion using standard flexible, medical grade plastic materials. Further details of the guide tube 12 will be described later.

The handle 14 may be constructed, for example, from molded plastic. The handle 14 is sized to be conveniently held by a clinician, to introduce the guide tube 12 into an interior body region that has been targeted for treatment.

As used in this disclosure, the term "proximal" refers to the aspect of the device that is, in use, held by the clinician, while the term "distal" to the aspect of the device that is, in use, positioned in or toward the body.

The purpose of the guide device 10 is to establish an open path through which an operative tool 16 can be deployed for use. For this purpose (see FIG. 2), the guide device 10 includes an interior guide passage 18. The guide passage 18 extends through an interior portion of the handle 14 continuously into and through the guide tube 12. Entrance into the guide passage 18 is provided by a proximal opening 20 formed in the handle 14. The guide passage 18 terminates at an opening 22 at the distal end of this guide tube 12. Further details of the configuration of the guide passage 18 will be described later.

As FIG. 2 shows, the guide passage 18 is sized and configured so that, in use, the operative tool 16 can be inserted through the proximal opening 20 and advanced through the passage 18 outwardly beyond the distal opening 22. Use of the guide device 10 in this manner facilitates deployment and positioning of the operative tool 16 that, by construction, may be less flexible and harder to manipulate than the guide tube 12 itself.

The guide tube 12, while flexible, preferable has a plastic memory or bias that normally orients the distal end region of the guide tube 12 in an essentially straight configuration, as shown in FIG. 1. To enable greater control of the orientation of the distal end region of the guide tube 10, the guide device 10 includes a steering assembly 24. In operation, the steering assembly 24 deflects the distal end region of guide tube 12 out of its essentially straight configuration and into a bent or deflected configuration, as shown in FIG. 3.

In its essentially straight configuration, the guide tube 12 is well oriented for deployment into an interior body region, e.g., through an intra-vascular or cannulated access path. During such deployment, the guide tube 12 may be passed over a conventional guide wire, which can be inserted through the interior passage 18. Or alternatively, the guide tuba 12 may be used with a dilator 60 (see FIG. 1A) which may be inserted through the interior guide passage 18. The dilator 60 features a tapered nosecone 62 on its distal end, a Luer type connector 64 on its proximal end, and a shaft 66 coupling the nosecone 62 to the Luer connector 64. The dilator 60 desirably includes a guide wire lumen 68 extending throughout the length of the dilator. In use, the tapered nosecone 62 extends past the distal tip or opening 22 of the steerable guide catheter 10 to facilitate access to the intra-vascular or cannulated access path and provide improved tracking onto the guide wire.

Upon deployment of the guide tube 12 to a desired body region (and withdrawal of the guide wire and dilator 60, if used), a clinician can operate the steering assembly 24 to deflect the distal end region of the guide tube 12 in its bent or deflected condition. A radiopaque marker M (see FIG. 3) can be placed on the distal end region to permit fluoroscopic visualization of the orientation of the deflected end region. In its bent or deflected configuration, the distal passage end 22 can be oriented in a desired relationship with a targeted tissue surface in the body region.

Desirably—as FIGS. 5A, 5B, and 5C show—the radiopaque marker M forms a partial ring (i.e., C-shaped) or comparable shape that changes depending upon orientation, so that the radiopaque image is visually distinct when observed in different orientations, e.g., presenting an upward U-shape when in an anterior orientation (FIG. 5A); or a downward U or "little-N" shape when in a posterior orientation (FIG. 5B); or an edge-on shape when in a lateral orientation (FIG. 5C). It should be appreciated that multiple radiopaque markers can also be used to provide an image which is visually distinct when observed in different orientations.

Desirably (as FIG. 3 shows), the guide tube 12 is placed into its bent or deflected configuration before passage of the operative tool 16 through the passage 18. Once in its bent or deflected configuration, as FIG. 4 shows, the operative tool 16 can be advanced through the passage 18 and guided by the bent configuration into the desired relationship with the tissue surface for use.

The steering assembly 24 holds the distal end of the guide tube 12 in its deflected condition, thereby maintaining the operative tool 16 in its desired relationship during use. The steerable guide tube 12 obviates the need to equip the operative tool 16 with an on-board steering mechanism or a guide wire lumen.

As FIGS. 3 and 4 show, the steering assembly 24 is desirable configured for single handed operation by the clinician. The steering assembly 24 is also desirably configured to provide a mechanical advantage sufficient to translate relatively small increments of clinician control into relatively larger increments of guide tube deflection.

As will be described in greater detail later, and as FIG. 3 generally shows, the steering assembly 24 includes an actuator 26 that can be manipulated by the clinician. The actuator 26 is coupled through a linkage system 28 to a deflecting component 30, which is coupled to the distal end region of the guide tube 12.

In general operation, manual force applied by the clinician to the actuator 26 is translated by the linkage system 28 into a pulling force or tension exerted on the deflecting component 30, which deflects or bends the distal end region of the guide tube 12. The linkage system 30 is desirably configured with a mechanical advantage that amplifies relatively small increments of movement of the actuator 26 into relatively larger increments of movement of the deflecting component 30.

Further details of particular embodiments of the guide tube 12 and the steering assembly 24 will now be described.

A. Components of the Guide Tube

Referring to FIGS. 6A and 6B, in the illustrated embodiment, the guide tube 12 comprises a main lumen 32, which constitutes a portion of the interior passage 18, already described. The guide tube 12 also includes a control lumen 34. The deflection component 30, previously described, extends through the control lumen 34.

Figure 6C:
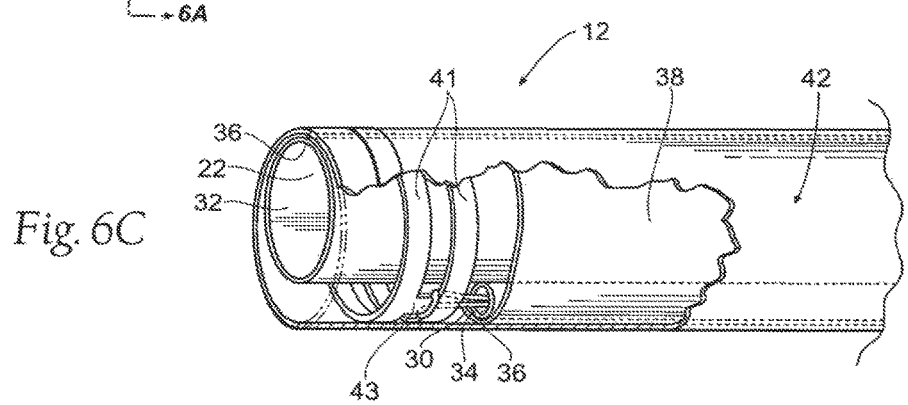
FIG. 6C is a perspective end view, partially broken away, of an alternative embodiment of the distal end region of the device shown in FIG. 6B.
Figure 6D:
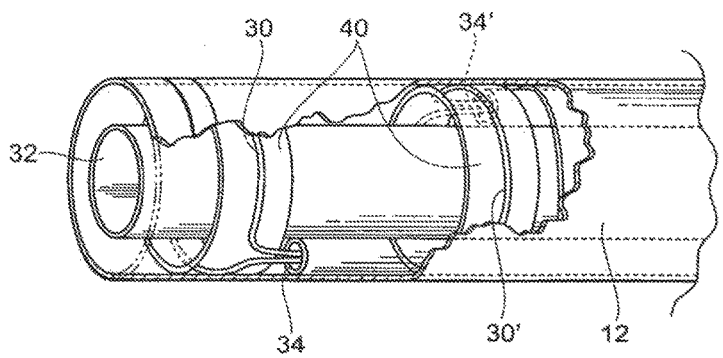
FIG. 6D is a perspective end view, partially broken away, of the distal end region of an alternative embodiment of the device shown in FIG. 6A, and showing multiple control lumens to direct the distal end region in more than one direction.
Figure 6E:
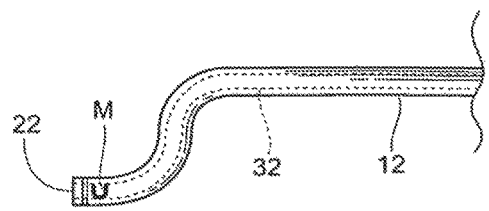
FIG. 6E is a plane view of the distal end region of the alternative embodiment shown in FIG. 6D, and showing the distal end region having two 90 degree deflections.

The illustrated embodiment shows one control lumen 34 and one deflection component 30. It should be appreciated that multiple control lumens (and deflection components) can be provided, if desired. As can be seen in FIGS. 6D and 6E, multiple control lumens would provide the ability to direct the flexible guide tube 12, (e.g., the distal end region) of the steerable guide 10 in more than one direction. For example, two control lumens 34, 34' oriented 180 degrees apart (along with two deflection components 30, 30') would allow the distal end region to be deflected 90 degrees in two directions within one plane. This feature would allow for additional steering control to accurately position the distal opening 22 at the targeted tissue site.

In the illustrated embodiment, the control lumen 34 is also shown to extend outside the main lumen 32. It should be appreciated that the control lumen 34 can extend inside the main lumen 32, or the main lumen 32 and the control lumen 34 can be formed as a composite.

Both the main lumen 32 and the control lumen 34 desirably include a liner 36. Each liner 36 preferably comprises a material with a low coefficient of friction, such as PTFE, although other materials having comparable mechanical properties can be used. The presence of the liner 36 in the main lumen reduces friction to ease the passage of the operative device 18 through the main lumen 32. The presence of the liner 36 in the control lumen 34 reduces friction and this moderates the pulling force or tension necessary to manipulate the deflecting component 30.

The guide tube 12 also desirably includes a reinforcement sheath 38. The reinforcement sheath 38 envelopes both the main lumen 32 and control lumen 34. The reinforcement sheath 38 can have multiple shape configurations, can be made of multiple materials, and can be arranged in multiple patterns. Patterns can range from a simple coil to a complex braid arrangement. The pattern can be uniform or can vary along the length of the catheter tube 12. In the illustrated embodiment, the reinforcement sheath 38 is in the form of a braid made of round wire made, e.g., from stainless steel, titanium, cobalt alloys, polymers, and natural fibers.

The guide tube 12 also desirably includes a tip reinforcing element(s) 40. The reinforcing element 40 is disposed at or near the distal opening 22 of the passage 18, and serves to resist collapse or distortion of the main lumen 32 during deflection as a result of pulling on the deflecting component 30.

In a desired embodiment, (see FIG. 6B), the tip reinforcing element 40 comprises a metallic ring, such as a uniform ring, but other shapes and materials are also contemplated. As seen in FIGS. 6A and 6B, the tip reinforcing element 40 is shown disposed over the reinforcement sheath 38. Alternatively, the tip reinforcing element 40 and the reinforcement sheath 38 can comprise a composite structure.

In the desired embodiment, the deflecting component 30 makes a continuous loop completely around the tip reinforcing element 40 and returns back through the control lumen 34 into the handle 14, where it is coupled to the linkage system 28, as will be described in greater detail later. In an alternative embodiment (see FIG. 6C), the deflecting component 30 loops around only a portion of a reinforcing element 41. As shown, the reinforcing element 41 comprises more than one ring (i.e., two or more individual rings) coupled together with at least one coupling element 43. In this configuration, the deflecting component 30 may be looped around one or more coupling element(s) 43.

The guide tube 12 also desirably includes a cover 42. The cover 42 envelopes all of the internal structures heretofore described, forming a composite structure. The cover 42 can be made of different types of material or of a uniform material with different physical characteristics throughout the length of the guide tube 12. The cover 42 can be of uniform thickness, or the thickness can vary along the length of the guide tube 12. In a preferred embodiment, the cover is made of a polymer material of differing hardness. The softest portion is located at the distal portion of the guide tube 12 (near the opening 22) and the stiffer portion is located at the proximal portion of the guide tube 12 (within the handle 14). The cover 42 can also include a material within the polymer which allows the cover 42 to be radiopaque or a material that reduces friction.

The tip reinforcing element 40, 41 and/or reinforcement sheath 38 can also be used as radiopaque markers. Alternatively, or in combination, one or more radiopaque markers M can be attached to the distal end of the catheter assembly 12. The use of radiopaque materials makes it possible to gauge the deflected orientation of the guide tube 12. A given radiopaque marker can made from platinum. Still, other materials (and different shapes) can be used.

As FIG. 7 shows, the guide tube 12 extends into the distal and of the handle 14. A transition shaft 44 is connected at one end to the proximal end of the guide tube 12 (where the cover 42 is stiffer) and at the other end to a sealing element 46 that occupies the proximal-most region of the handle 14. The sealing element 46 includes an interior lumen 48 that comprises an extension of the interior passage 18, and also includes the proximal opening 20. The transition shaft 44 also includes an interior lumen 50 that also forms an extension of the interior passage 18, linking the main lumen 32 of the guide tube 12 in communication with the proximal opening 20. The transition shaft 44 can be an integrated component of the guide tube 12.

The sealing element 46 desirably includes an in-line hemostatic valve assembly 52 at or near the proximal opening 20 of the passage 18. The valve assembly 52 prevents blood or fluid loss by sealing the proximal opening 20 when an operative tool 16 is within the passage 18, as well as when no operative tool 16 is present in the passage 18.

The valve assembly 52 desirably includes a main seal component 54 and a lip seal component 56, which can comprise separate or integrated components. The main seal component 54 seals the proximal opening 20 in the absence of an operative tool 16 in the passage 18. The lip seal component 56 seals upon insertion of the operative tool 16 through the proximal opening 20 into the passage 18.

An infusion valve 58 can also be coupled to the passage 18 through the sealing element 46. In this way, fluid can be conveyed through the passage 18 into the interior body region, e.g., to flush materials from the passage 18 during use.

As described, the guide tube 12 is secured to the handle 14 and does not rotate relative to the handle 14. To rotate the guide tube 12, the clinician must rotate the handle 14.

B. Components of the Steering Assembly

1. The Actuator

It should be appreciated that the actuator 26 of the steering assembly 24 can take many forms, such as a sliding lever or a pistol grip. The actuator 26 can be located at many locations on the handle 14, such as the proximal end, the distal end, or the mid-portion. In the embodiment shown in FIGS. 1 to 4, the actuator 26 takes the form of a fluted knob that is rotationally attached to the distal end of the handle 14. The knob 26 is positioned so that it can be rotated by the thumb of the clinician's hand that holds the handle 14. As shown in FIG. 3, the handle 14 may be held in the palm of the hand while the knob 26 is manipulated by the thumb.

Figure 9:
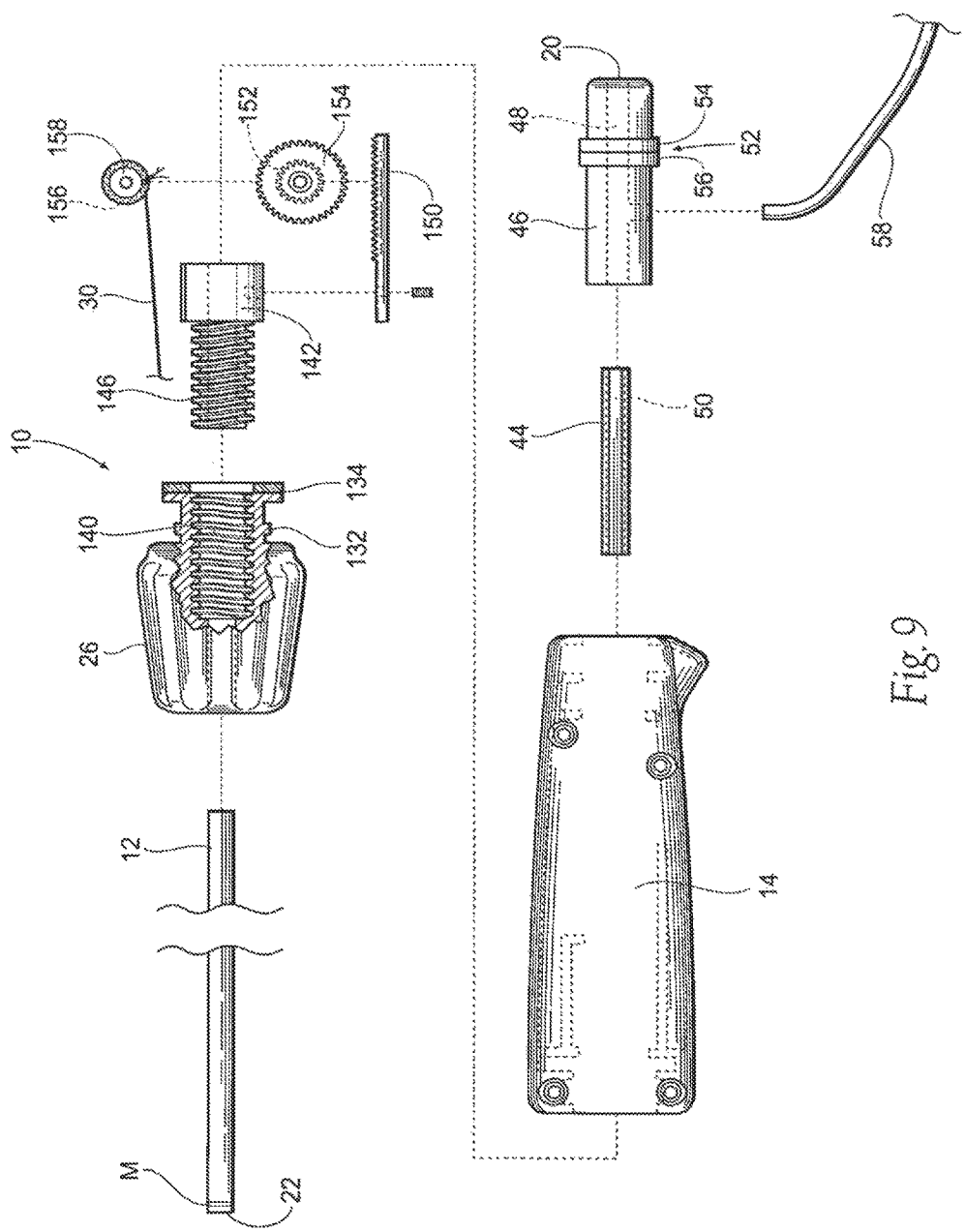
FIG. 9 is an exploded view, with parts partially broken away and in section, showing the main components of the device, including the components of the steering assembly shown in FIG. 8.

In the illustrated arrangement (best shown in FIGS. 8 and 9), the knob 26 includes front and rear thrust bearing surfaces 132 and 134. These thrust bearing surfaces can be integral to the knob component or they can be separate components which are added to the knob 26 to make a complete assembly. Front and rear journals 136 and 138 on the handle 14 support the thrust bearing surfaces 132 and 134, so that the knob 26 can be easily rotated relative to the distal end of the handle 14 by movement of the thumb.

2. The Linkage System a. Rack and Pinion Gear Assembly

In the illustrated arrangement, the linkage system 28 translates rotational movement of the actuator knob 26 into a linear force direction. To affect this translation (see FIGS. 8 and 9), the linkage system 28 includes a female threaded shaft 140 formed within the knob 26, which rotates in common with the knob 26, and a threaded male component 146 that is coupled to a slider 142, which is mounted for linear movement in a channel 144 within the handle 14. It should be appreciated that the thread placement on both of these elements could be reversed. The threads can take any form and/or type, and can be self-locking or non-locking. In a preferred arrangement, the threads on the female threaded shaft 140 and the male threaded component 146 are locking.

The slider 142 is restrained by the channel 144 from twisting or rotating. Coupled to the slider 142, which is kept from twisting or rotating within the channel 144, the threaded component 146 is likewise kept from rotation.

The threaded male component 146 extend from the slider 142 in the direction of the knob 26. The male threads on the component 146 are configured to thread into the female threads of the shaft 140 in response to rotation of knob 26. Rotation of the knob 26 progressively moves the threaded component 146 within the shaft 140. The slider 146 follows, moving in a linear direction within the channel 144 fore (toward the distal end of the handle 14) or aft (toward the proximal end of the handle 14), depending upon the direction the knob 26 is rotated. Aft linear movement of the slider 142 within the channel 144 is halted by a proximal stop 148. This position (i.e., when the slider 142 rests in abutment against the stop 148) (as shown in FIG. 8) will be called in shorthand a "neutral position," because, in this position, the linkage system 28 is configured to apply no force upon the deflecting component 30.

When in the neutral position (as shown in FIG. 8), the male component 146 extends from the slider 142 a distance sufficient to thread a portion of the male component 146 within a portion of female threads of the shaft 140. When in the neutral position, rotation of the knob 26 in a single predetermined direction (in the illustrated embodiment, clockwise from the clinician's view point) (see FIG. 11) advances the component 146 along the shaft 140 and draws the slider 142 in a linear forward direction within the channel 144 (i.e., toward the knob 26). It should be appreciated that the direction for activation could be reversed (i.e., rotating the knob 26 advances the slider 142 in a linear direction away from the knob 26).

The linkage system 28 is configured to translate this linear forward movement of the slider 142 into a tension or pulling force on the deflecting component 30. To affect this translation, the linkage system 28 includes a rack and pinion gear system. More particularly (see FIGS. 8 and 9), a rack 150 is coupled to slider 142 for linear movement in common with the slider 142. In the illustrated embodiment, the rack 150 extends in a direction away from the knob 26, into the more proximal region of the handle 14. There (as also shown in FIG. 10), the rack 150 engages a pinion gear 152. The pinion gear 152 is coupled to a main gear 154, which is supported for rotation on a shaft within the handle 14. The main gear 154 is, in turn, coupled through another pinion gear 158 to a pick up reel 56, which is likewise supported for rotation on a shaft within the handle 14. The proximal end of the deflecting component 30 is coupled to the pick up reel 156. The attachment can be accomplished, e.g., by crimping, tying, or adhesion.

Rotation of the pick up reel 156 in a predetermined direction (which, in the illustrated embodiment, is counterclockwise) applies a linear aft pulling force or tension upon the deflecting component 30, thereby bending the distal end region of the catheter tube 12.

In an alternative arrangement (not shown), a spiral cut gear coupled to the knob could engage the rack to move the rack in a linear direction in response to rotation of the knob.

As FIG. 11 best shows, the linkage system 28, as described, translates rotation of the knob 26, which draws the slider 142 toward the knob 26, into linear forward translation of the rack 150. Linear forward translation of the rack 150 is, in turn, translated into rotation of the pinion gear 152 (which, in the illustrated embodiment, is clockwise). Rotation of the pinion gear 152 translates into an opposite rotation (i.e., counterclockwise) of the main gear 154. Rotation of the main gear 154 translates into an opposite rotation (i.e., clockwise) of the pinion gear 158. Rotation of the pinion gear 158 translates into an opposite rotation (i.e., counterclockwise) of the pick up reel 156. Rotation of the pick up reel 156 is, in turn, translated into a linear aft pulling force or tension on the deflecting component 30, to deflect the distal end of the guide tube 12.

The gear ratio of the rack 150 and the main gear 154, as well as the diameter of the main gear 154, are selected, taking into account the size constraints imposed by the handle 14, to provide a desired mechanical advantage. The mechanical advantage amplifies the incremental amount of deflection of the deflection component 30 for a given increment of rotation of the knob 26. Due to the mechanical advantage, the amount of manual, thumb-applied force required to rotate the knob 26 is, to the clinician, normal and without strain. Deflection of the guide tube 14 occurs with comfortable thumb control.

b. Pivot Tensioning System

FIGS. 12 and 13 show an alternative arrangement for the steering assembly 24. The alternative arrangement shown in FIGS. 12 and 13 shares many of the functional components of the arrangement shown in FIG. 8. Both include the rotary actuator knob 26 that carries the internal female threaded shaft 140, and a slider 142 that carries the threaded male component 146, which threadably engages the threaded shaft 140.

Also as before described, and as shown in FIG. 13, rotation of the actuator knob 26 is translated into linear movement of the slider 142 within the channel 144 inside the handle 14. In the rack and pinion linkage arrangement shown in FIG. 11, distal movement of the slider 144 (toward the knob 26) serves to apply tension to the deflecting component 30 through the rotation imparted to the take up reel 156 by the lateral movement of the rack 150 attached to the slider 144. In the alternative arrangement shown in FIGS. 12 and 13, proximal movement of the slider 142 (away from the knob 26) applies tension to the deflection component 30 through a tension arm 160 that pivots in a proximal direction along the longitudinal axis of the handle 14. The deflecting component 30 is attached to the pivoting tension arm 160 and is placed into tension as a result of the proximal pivoting movement, to bend the distal region of the catheter tube 12, as FIG. 13 shows.

More particularly, the tension arm 160 is mounted on a pin 162 within the housing 14 for pivoting between a first pivot position, leaning distally toward the knob 26 (see FIG. 12) and a second pivot position leaning proximally away from the knob 26 (see FIG. 13). In the first pivot position (FIG. 12), no tension is applied to the deflecting component 30 attached to the tension arm 160. In the second pivot position (FIG. 13), the deflecting component 30 is placed into tension, to bend or deflect the distal end region of the guide tube 12.

When in the first pivot position (FIG. 12), the pivoting tension arm 160 rests against the proximal end of the slider 142. As the knob 26 is rotated in a predetermined direction (which, in the illustrated embodiment (FIG. 13), is counter-clockwise from the standpoint of the clinician), the slider 142 is moved in a linear direction away from the knob 26. The slider 142 pushes against the tension arm 160, causing it to pivot about the pin 162 into the second pivot position. Pivoting of the tension element translates into a linear proximal pulling force or tension on the deflecting component 30, to deflect the distal end of the guide tube 12.

Translating the linear movement of the slider 142 into rotational movement of the pivoting tension arm 160 reduces the mechanical force advantage of the overall system, while increasing the amount of deflection of the distal end region per given rotation of the rotary control element.

3. The Deflection Component

The deflecting component 30 extends from the pick up reel 156 or pivoting tension arm 160 end into the control lumen 34 of the guide tube 12. The deflecting component 30 desirably comprises a strong and flexible material, e.g., metallic wire, braided metallic wire, monofilament wire, etc. In a preferred arrangement, the deflecting element 30 comprises a continuous length of braided polymer or natural fiber. The fiber extends from the pick up reel 156 or pivoting tension arm 160, through the control lumen 34, looping completely around the tip reinforcing element 40, as FIG. 6B best shows. From there, the fiber extends back through the control lumen 34 to terminate at the pick up reel 156 or pivoting tension arm 160.

In this arrangement, the deflecting conponent 30 can be attached to the tip reinforcing element 40 by various methods, such as adhesion, welding techniques, soldering techniques, tying or wrapping the deflection component 30 to the tip reinforcing element 40, or by forming the deflecting component 30 and the tip reinforcing element 40 as a composite structure. In the alternative embodiment shown in FIG. 6C, separate attachment means may not be necessary to connect the deflecting component 30 to the tip reinforcing element 41.

II. Use of Steerable Guide Device

Figure 14:
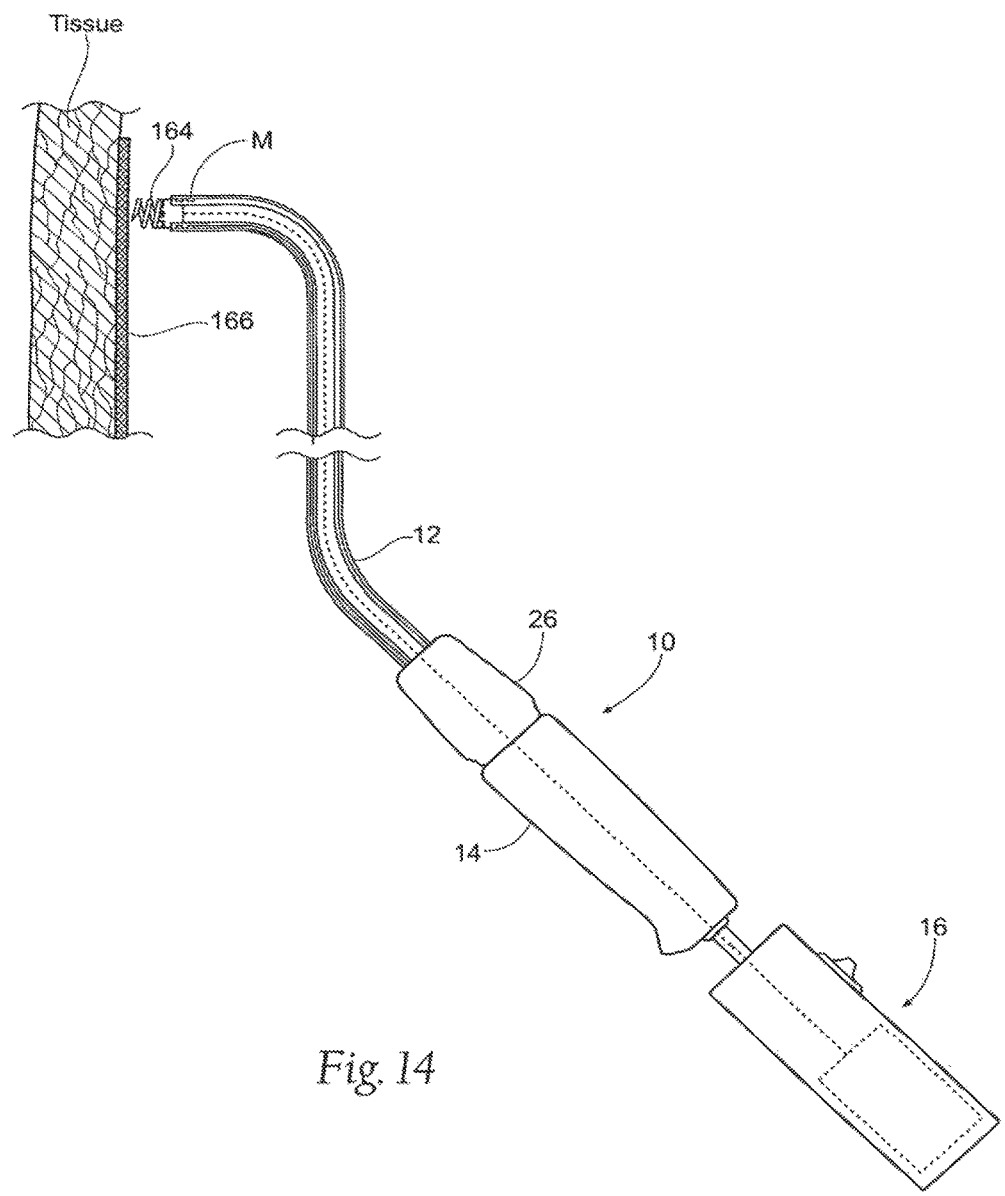
FIG. 14 is a side view of the steerable guide device and associated operative tool, as also generally shown in FIG. 4, with the operative tool shown to be an endovascular fastener oriented by the guide device or the application of a fastener to a prosthesis deployed in a tissue region.

FIG. 14 shows the steerable guide device 10 in use to guide an operative tool 16 to a tissue site. In FIG. 14, the operative tool 16 takes the form of a powered device that applies a helical fastener 164. A representative embodiment of an endovascular device that, in use, applies a helical fastener is described in U.S. patent application Ser. No. 10/786,465, and entitled "Systems and Methods for Attaching a Prosthesis Within a Body Lumen or Hollow Organ," which is incorporated herein by reference. In use (as FIG. 14 shows), the endovascular fastener device 16 is manipulated through the guide device 10 to apply one or more fasteners 164 to a prosthesis 166 that is deployed to repair diseased and/or damaged sections of a hollow body organ and/or a blood vessel, e.g., to repair an aneurysm in the aorta in the region between the heart and the iliac bifurcation.

In use, the steerable guide device 10 is introduced to the targeted tissue site through a conventional intravascular approach. For example, when the targeted tissue site is in the aorta, the guide device 10 can be introduced through the femoral artery. However, other access sites and methods can be utilized. The guide device 10 is desirably introduced over a guide wire, which extends through the passage 18. The guide wire can comprise the same guide wire over which the prosthesis 166 has been previously introduced, by means of a separately deployed prosthesis introducing tool. Or alternatively, introduction of the steerable guide device 10 can be accomplished through a separate access site.

Upon withdrawal of the prosthesis introducing tool over the guide wire, and under fluoroscopic visualization, the clinician tracks the guide device 10 and dilator 60 over the same guide wire to locate the distal end region of the device 10 at or near the desired location with respect to the prosthesis. The guide wire and dilator 60 can now be withdrawn. Actuating the steering assembly 24 (by rotating the knob 26), and still employing fluoroscopy visualization, the clinician deflects the distal end region of the device 10—and rotates the handle 14 to rotate the catheter tube 12, if necessary—to orient the distal opening 22 of the passage 18 in a desired facing relationship with the site where introduction of a fastener 164 is desired.

The operative tool 16, e.g., the endovascular fastener device, is now inserted through the proximal opening 20 and advanced through the passage 18 until the fastener 164 is located for deployment outside; the now-oriented distal opening 23, as FIG. 14 shows. The operative tool 16 can be actuated to apply a fastener 164 to the prosthesis 166. If the operative tool 16 is a singles fire device, i.e., it carries only one fastener 164, the operative tool 16 is withdrawn through the passage 18 and a new fastener 164 mounted. The distal end region of the device 10 is reoriented in facing relationship with a new fastening site. The operative tool 16 is inserted back through the passage 18 to apply the second fastener to the new fastening site. This sequence is repeated until a desired number and array of fasteners 164 are applied to the prosthesis 166. At this point, the guide device 10 can be withdrawn.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A guide device comprising:
   a flexible guide tube comprising a main lumen defining a guide passage and at least one control lumen separate from the main lumen, the guide tube further comprising a tip reinforcing element comprising a uniform ring;
   a handle coupled to the guide tube, the handle comprising a proximal opening in communication with the guide passage through which a separate operative tool can be advanced; and
   a steering assembly comprising:
   a deflecting element at least partially within the control lumen and coupled to a distal end region of the flexible guide tube to apply a deflecting force to bend the distal end region, the deflecting element making a continuous loop completely around the tip reinforcing element,
   an actuator configured to rotate about the longitudinal axis of the guide device and rotatable by a single-handed operation, and
   a linkage system coupling the actuator to the deflecting element to apply the deflecting force in response to operation of the actuator, the linkage system including a slider and a pivoting lever arm, the slider having a threaded portion adapted to mate with a threaded portion of the actuator, the pivoting lever arm directly coupled to a proximal end of the deflecting element at a first end portion and pivotally attached to the handle at a second end portion and adapted to be contacted by the slider to translate rotation of the actuator into linear movement of the slider into pivotal movement of the lever arm to apply the deflecting force to the deflecting component, wherein the linkage system is positioned within the handle and amplifies the amount of deflecting force.

2. The device according to claim 1 further comprising at least one additional deflecting element.

3. The guide device according to claim 1 further comprising at least two control lumens.

4. The guide device according to claim 3 wherein the control lumens are oriented 180 degrees apart.

5. The guide device according to claim 1 wherein the distal end region of the guide tube comprises radiopaque markers.

6. A system comprising:
   a guide device as defined in claim 1, and
   an operative tool that applies one or more fasteners to tissue.

7. A method comprising:
   providing a guide device as defined in claim 1,
   deploying the guide device into an interior tissue region, and
   operating the steering assembly to bend the distal end region of the guide tube.

8. A method comprising:
   providing a system as defined in claim 6,
   deploying the guide device into an interior tissue region,
   operating the steering assembly to bend the distal end region of the guide tube,
   passing the operative tool through the guide device, and
   operating the operative tool while residing in the guide device to apply at least one fastener to tissue.

* * * * *